US010508989B2

(12) United States Patent
Stockwell et al.

(10) Patent No.: US 10,508,989 B2
(45) **Date of Patent: *Dec. 17, 2019**

(54) OPTICAL CHEMICAL ANALYSER AND LIQUID DEPTH SENSOR

(71) Applicant: International Moisture Analysers Limited, Leeds (GB)

(72) Inventors: Paul Stockwell, Tadley (GB); David Widdup, Wokingham (GB); Michael Foster, London (GB); Jonathan Storey, Tonbridge (GB)

(73) Assignee: International Moisture Analysers Limited, Leeds (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/035,587

(22) Filed: Jul. 14, 2018

(65) Prior Publication Data

US 2018/0348125 A1 Dec. 6, 2018

Related U.S. Application Data

(63) Continuation of application No. 14/758,914, filed as application No. PCT/GB2014/050050 on Jan. 9, 2014, now Pat. No. 10,041,880.

(51) Int. Cl.
*G01N 21/45* (2006.01)
*G01N 21/65* (2006.01)
(Continued)

(52) U.S. Cl.
CPC ............ *G01N 21/45* (2013.01); *G01J 3/4412* (2013.01); *G01J 3/45* (2013.01); *G01N 21/65* (2013.01);
(Continued)

(58) Field of Classification Search
CPC ........ G01N 21/45; G01N 21/65; G01N 21/85; G01N 21/8507; G01J 3/4412; G01J 3/45
See application file for complete search history.

(56) References Cited

U.S. PATENT DOCUMENTS 3,923,403 A 12/1975 Harklau
3,964,867 A 6/1976 Berry
(Continued)

FOREIGN PATENT DOCUMENTS

CN 1092981 A 10/1994
CN 201724904 U 1/2011
(Continued)

OTHER PUBLICATIONS

Foreign Communication from a Related Counterpart Application, International Search Report dated Jul. 7, 2014, International Application No. PCT/GB2014/050050.
(Continued)

*Primary Examiner* — Hina F Ayub

(57) ABSTRACT

An optical chemical analyser comprises a source of a first amount of radiation (46), an optics module configured to direct the first amount of radiation such that it is incident on or passes through a target (14) at a target location, the optics module further being configured to receive a second amount of Raman scattered radiation from the target and direct the second amount of radiation (206) to a Spatial Interference Fourier Transform (SIFT) module, the SIFT module including a first dispersive element (216) and a second dispersive element (218), the SIFT module being configured such that a portion of the second amount of radiation is received by the first dispersive element and interferes with a portion of the second amount of radiation received by the second dispersive element to form an interference pattern; the SIFT module further comprising a detector (48) configured to capture an image of at least a portion of the interference
(Continued)

pattern and produce a detector signal (226) based on the captured image; and a processor configured to receive the detector signal from the detector and perform a Fourier transform on the detector signal to thereby obtain a frequency spectrum of the second amount of radiation.

22 Claims, 12 Drawing Sheets

(51) Int. Cl.
*G01J 3/44* (2006.01)
*G01N 21/85* (2006.01)
*G01J 3/45* (2006.01)

(52) U.S. Cl.
CPC ......... *G01N 21/85* (2013.01); *G01N 21/8507* (2013.01)

(56) References Cited

U.S. PATENT DOCUMENTS

| | | | | |
|---|---|---|---|---|
| 4,873,863 | A | 10/1989 | Bruhl et al. | |
| 5,073,024 | A | 12/1991 | Valette | |
| 5,367,175 | A | 11/1994 | Bobb | |
| 6,359,687 | B1 | 3/2002 | Cheng | |
| 6,687,007 | B1 | 2/2004 | Meigs | |
| 8,130,386 | B1 | 3/2012 | Hayashida et al. | |
| 2002/0072677 | A1 | 6/2002 | Sevick-Muraca | |
| 2004/0071325 | A1 | 4/2004 | Joseph Declerck | |
| 2005/0106746 | A1 | 5/2005 | Shinn et al. | |
| 2006/0238764 | A1 | 10/2006 | Hafeman | |
| 2009/0273776 | A1 | 11/2009 | Bittner | |
| 2011/0000296 | A1 | 1/2011 | Muerset | |
| 2013/0188181 | A1 | 7/2013 | Angel et al. | |
| 2013/0335302 | A1 | 12/2013 | Crane | |
| 2014/0081594 | A1* | 3/2014 | Tunheim | G01N 21/31 702/150 |
| 2014/0247447 | A1* | 9/2014 | Angel | G01J 3/44 356/301 |
| 2015/0233812 | A1* | 8/2015 | Yan | G01N 15/1434 250/214.1 |
| 2015/0247950 | A1 | 9/2015 | Perkins | |
| 2015/0285733 | A1* | 10/2015 | Henriksen | G01N 21/15 134/1 |
| 2015/0338351 | A1 | 11/2015 | Stockwell et al. | |
| 2016/0054343 | A1 | 2/2016 | Holmes | |

FOREIGN PATENT DOCUMENTS

| | | | |
|---|---|---|---|
| CN | 201897503 | | 7/2011 |
| CN | 201974383 | U | 9/2011 |
| CN | 202057580 | U | 11/2011 |
| CN | 102419198 | A | 4/2012 |
| DE | 19916072 | A1 | 10/2000 |
| EP | 0239772 | A2 | 10/1987 |
| EP | 1054250 | A | 11/2000 |
| EP | 2215452 | B1 | 9/2016 |
| FR | 2713766 | A1 | 6/1995 |
| GB | 2147697 | | 5/1985 |
| GB | 2193313 | A | 2/1988 |
| GB | 2203831 | A | 10/1988 |
| GB | 2254417 | A | 10/1992 |
| JP | 2003075647 | A | 3/2003 |
| JP | 2005352065 | A | 12/2005 |
| RU | 2075065 | C1 | 3/1997 |
| RU | 2181487 | C2 | 4/2002 |
| WO | 9307472 | A | 4/1993 |
| WO | 9900003 | | 1/1999 |
| WO | 2004110465 | A1 | 12/2004 |
| WO | 20090161729 | A1 | 5/2009 |

OTHER PUBLICATIONS

Gomer, M.R., et al., "Ramana Spectroscopy Using a Spatial Heterodyne Spectrometer: Proof of Concept", Applied Spectroscopy, vol. 65, No. 8, 2011, pp. 849-857, XP002726596.

Scott, A. et. al., "Improved coupling to integrated spatial heterodyne spectrometers with applications to space", Reliability, Packaging, Testing, and Nanodevices X, SPIE 1000 20th St. Bellingham WA, 98225-6705 USA, vol. 7928, No. 1, Feb. 10, 2011 (Feb. 10, 2011, pp. 1-10, XP060006542.

Office Action dated May 2, 2017, U.S. Appl. No. 14/758,914, filed Jul. 1, 2015.

Examination Report dated Jun. 23, 2017, GB Application No. 1300371.0.

Notice of Allowance dated Mar. 26, 2018, U.S. Appl. No. 14/758,914, filed Jul. 1, 2015.

Corrected Notice of Allowability dated Jul. 6, 2018, U.S. Appl. No. 14/758,914, filed Jul. 1, 2015.

* cited by examiner

OPTICAL CHEMICAL ANALYSER AND LIQUID DEPTH SENSOR

CROSS-REFERENCE TO RELATED APPLICATIONS

This application is a continuation of and claims priority under 35 U.S.C. § 120 to U.S. patent application Ser. No. 14/758,914, filed on Jul. 1, 2015, entitled "OPTICAL CHEMICAL ANALYSER AND LIQUID DEPTH SENSOR", by Paul Stockwell, et al., which is a filing under 35 U.S.C. 371 as the National Stage of International Application No. PCT/GB2014/050050, filed Jan. 9, 2014, which claims priority to GB Application No. 1300371.0 filed with the Intellectual Property Office of the United Kingdom on Jan. 9, 2013, all of which are incorporated herein by reference in their entirety for all purposes.

SUMMARY

The present invention relates to an optical chemical analyser and a liquid depth sensor. In particular, the invention relates to an optical chemical analyser and a liquid depth sensor which may be attached to a fluid vessel, for example a gas pipeline.

Gas pipelines form part of a National Transmission System (NTS) for conveying gas from entry points to exit points. Entry points may include coastal terminals, treatment facilities and storage facilities. Exit points may include connections to distribution networks, large consumers and further storage sites.

The presence of contaminants within gas pipelines has been a problem for some time.

For example, each year there are several serious incidents of liquid contamination within gas pipelines of the NTS, some of which cause damage to gas equipment which forms part of the NTS or the equipment of large industrial customers. The annual bill to repair damage and compensate customers in the UK alone is considered to be in excess of £1M.

There are three main suspected mechanisms for liquid contamination.

First, gas producers (i.e. those who supply gas to the NTS via feed points) may accidentally allow liquids (e.g. glycols, methanol, amines, water or gas condensates) to contaminate the gas. This may occur for several reasons. Glycol dehydration is a well known method for removing unwanted water from gas. Examples of glycols which may be used include triethylene glycol (TEG) and ethylene glycol (MEG). The glycols are injected into the gas so that they can dehydrate the gas and then the glycols are subsequently removed from the gas. In a similar manner, amines may be added to the gas to remove unwanted hydrogen sulphide and carbon dioxide. Methanol may be added to lower the risk of hydrate formation. On some occasions the removal of added methanol and/or amines may not be complete leaving them to remain within the gas as a liquid contaminant. In addition, heavier hydrocarbon condensates (for example, those with a carbon chain length of six or more) may be present within the gas.

Secondly, gas within the NTS may have a composition such that a component of the gas under certain physical conditions (e.g. change in temperature, pressure and/or flow) condenses out of the gas as liquid contaminant in an unexpected manner.

Thirdly, an operational problem with a compressor station which forms part of the NTS may cause leakage of compressor oil into a gas pipeline.

The chemical analysers currently used to monitor gas for contaminants at entry points to the NTS and within the NTS are gas phase systems—that is to say, they only detect the presence of gaseous species. Consequently, liquid contaminants may not be detected by the analysers and/or the presence of liquid contaminants within the gas may cause damage to the analysers or require that the analysers undergo lengthy maintenance. If an analyser is damaged or requires maintenance then this can take critical measurement systems offline until repairs can be performed. If the measurement systems are taken offline whilst the portion of the NTS covered by the measurement systems continues to operate then there will be no way of telling if contaminants are present in this portion of the NTS.

As previously discussed, failure to detect the presence of liquid contaminants within a gas pipeline of the NTS may result in damage to gas equipment which forms part of the NTS or damage to the equipment of large industrial customers.

It follows that, due to the current inability to detect the presence of liquid contaminants, it is also not possible to identify what liquid contaminants (if any) are present within a gas pipeline of the NTS.

It is an object of the present invention to obviate or mitigate problems with known chemical analysers and/or methods of detecting liquid contaminants whether described above or otherwise. It is a further object of the present invention to provide an alternative chemical analyser and/or an alternative liquid depth sensor.

According to an aspect of the present invention there is provided an optical chemical analyser comprising a source of a first amount of radiation, an optics module configured to direct the first amount of radiation such that it is incident on or passes though a target at a target location, the optics module further being configured to receive a second amount of radiation from the target and direct the second amount of radiation to a Spatial Interference Fourier Transform (SIFT) module, the SIFT module including a first dispersive element and a second dispersive element, the SIFT module being configured such that a portion of the second amount of radiation is received by the first dispersive element and interferes with a portion of the second amount of radiation received by the second dispersive element to form an interference pattern; the SIFT module further comprising a detector configured to capture an image of at least a portion of the interference pattern and produce a detector signal based on the captured image; and a processor configured to receive the detector signal from the detector and perform a Fourier transform on the detector signal to thereby obtain a frequency spectrum of the second amount of radiation.

The target may be located in a gas in a high pressure environment. A high pressure environment may be an environment in which the pressure is greater than about 3 bar and less than about 300 bar. In other embodiments the pressure may be greater than about 300 bar. In some embodiments the pressure may be about 70 bar.

The target may be located in a vessel, and, optionally, the vessel may be a gas pipeline.

The optical chemical analyser may be configured to be located at a stand-off position relative to the target location such that the distance along the beam path of each of the first and second amounts of radiation between the target location and any optical component of the optics module through which the first or second amounts of radiation pass in use is greater than about 30 cm. This enables the optical chemical analyser to be used, for example, in conjunction with pipelines of significant diameter in which a portion of the optical chemical analyser is mounted to the top of the pipeline and the target location is at the bottom of the pipeline.

The first amount of radiation may be substantially polychromatic; and the SIFT module may further comprise a third dispersive element and a fourth dispersive element, the SIFT module being configured such that a portion of the first amount of radiation is received by the third dispersive element and interferes with a portion of the first amount of radiation received by the fourth dispersive element to form a second interference pattern; the SIFT module further comprising a second detector configured to capture an image of at least a portion of the second interference pattern and produce a second detector signal based on the image captured by the second detector; and a processor configured to receive the second detector signal from the second detector and perform a Fourier transform on the second detector signal to thereby obtain a frequency spectrum of the first amount of radiation, the processor further being configured to compare the frequency spectrum of the second amount of radiation to frequency spectrum of the first amount of radiation in order to produce an absorption spectrum.

The processor may be configured to process the frequency spectrum of the absorption spectrum and thereby identify the presence (or, in alternative embodiments absence) of a substance in the target and/or determine a concentration of a substance in the target.

The first amount of radiation may be substantially monochromatic and substantially coherent.

The processor may be configured to process the frequency spectrum of the second amount of radiation and thereby identify the presence of a substance in the target and/or determine a concentration of a substance in the target.

The second amount of radiation may be Raman scattered radiation.

The optics module may further comprise a suppression filter configured to substantially prevent a component of the second amount of radiation which has a frequency which is substantially the same as a frequency of the first amount of radiation from reaching the SIFT module.

The optics module may include an optical fibre along which the first and second amounts of radiation are transmitted.

The SIFT module may comprise a beam splitting apparatus configured to split the second amount of radiation into: the portion of the second amount of radiation that is received by the first dispersive element, and the portion of the second amount of radiation received by the second dispersive element.

The first and second dispersive elements may be first and second diffraction gratings respectively and the plane of each of the first and second diffraction gratings may be non-perpendicular with respect to an optical axis of the portions of the second amount of radiation that are received by the first and second diffraction gratings respectively.

The detector may comprise a CCD or CMOS sensor.

The optical chemical analyser may further comprise a target detection module, the target detection module being configured to detect a change in presence of a desired class of target and output a target change signal when a predetermined change in presence of the desired class of target is detected.

The optical chemical analyser may be configured such that at least a portion of the optical chemical analyser enters a powered-up state from a powered-down state based on the target change signal being output by the target detection module.

The at least a portion of the optical chemical analyser which enters a powered-up state from a powered-down state may be the source of the first amount of radiation and/or the detector.

The target detection module may comprise a liquid depth sensor according to the second aspect of the present invention discussed below.

The controller of the liquid depth sensor may be configured to output the target change signal when a measure of a depth of a liquid exceeds a predetermined threshold.

The optical chemical analyser may further comprise a radiation directing element, the radiation directing element being configured to direct the second amount of radiation to the SIFT module, and direct the second amount of detection radiation to the sensor arrangement.

The radiation direction element may comprise a dichroic filter.

The optics module may be configured to direct the first amount of radiation so that the first amount of radiation passes through free space immediately before being incident on the target, and wherein optics module is configured such that the second amount of radiation from the target passes through the free space prior to the second amount of radiation being provided to the SIFT module.

The free space may comprise a fluid.

The optical chemical analyser may further comprise an imaging device.

The imaging device may be configured to produce an image of at least a portion of the target.

The optical chemical analyser may further comprise an imaging controller, the imaging controller being configured such that it selectively energises the imaging device based on the detector signal.

The optics module may be configured to direct the first amount of radiation through a volatile substance such that the first amount of radiation transfers energy to the volatile substance, and wherein the source of the first amount of radiation and the optics module are configured such that a total energy and/or a density of energy transferred to the volatile substance from the first amount of radiation is less than an ignition amount.

The target location may be at a portion of a filter (or filter arrangement) which is configured to filter (for example, reduce the amount of a contaminant within) a fluid passing through the filter. The target location may be at a surface of a filter element which forms part of the filter, the filter element being configured to reduce the amount of a contaminant within a fluid passing through the filter.

The target may be a fluid and the fluid may be contained in a vessel. In other embodiments the target may be a powder or dust. The powder or dust may be contained in a vessel.

The optical chemical analyser may be configured to be located exterior to the vessel.

The vessel may be a portion of a pipeline. The pipeline may be a gas pipeline. The gas pipeline may carry natural gas or compressed air.

The vessel may be a portion of a filter which is configured to filter a fluid passing through it.

The optical chemical analyser may further comprise a window which is configured to be mounted to the vessel, the window being substantially transparent to the first and second amounts of radiation, the source being configured such that, in use, the first and second amounts of radiation pass through the window.

The window may be formed from sapphire. The sapphire may be c-cut sapphire. The sapphire may be braised in place.

The optical chemical analyser may further comprising a heater, the heater being in thermal communication with said window and being configured to heat the window. The optical chemical analyser may further comprise a thermal insulator which thermally isolates the heater from the vessel.

The optical chemical analyser may further comprise a vent passage, a first end of which is configured to be in fluid flow communication with a portion of the window which is in fluid flow communication with the fluid contained in the vessel and a second end which is in fluid flow communication with the exterior of the vessel; the vent passage further comprising a closing member, which in a normal, closed configuration substantially prevents fluid flow between the first and second ends of the vent passage, and which in an open configuration allows fluid flow between the first and second ends of the vent passage.

According to a second aspect of the invention there is provided a liquid depth sensor suitable for use with a fluid pipeline, the liquid depth sensor comprising a radiation source producing a first amount of detection radiation, the radiation source being configured, in use, to direct the first amount of detection radiation so that it is incident on a liquid at a depth sensing location; a sensor arrangement arranged to receive a second amount of detection radiation, the second amount of detection radiation being a portion of the first amount of detection radiation which is reflected by the liquid, the position at which the second amount of detection radiation is incident on the sensor arrangement being dependent on a path length between the radiation source and a surface of the liquid, the sensor arrangement further being configured to output a sensor signal indicative of the position at which the second amount of detection radiation is incident on the sensor arrangement; and a controller configured to receive the sensor signal and determine a measure indicative of the depth of the liquid based on the sensor signal.

The controller may be configured to determine a measure indicative of the path length between the radiation source and a surface of the liquid based on the sensor signal.

The sensor arrangement may be arranged to receive a third amount of detection radiation, the third amount of detection radiation being a portion of the first amount of detection radiation which is reflected by a second surface, the position at which the third amount of detection radiation is incident on the sensor arrangement being dependent on a path length between the radiation source and the second surface, the sensor arrangement further being configured to output a sensor signal indicative of the position at which the third amount of detection radiation is incident on the sensor arrangement.

The controller may be configured to determine a measure indicative of the difference between the path length between the radiation source and a surface of the liquid and the path length between the radiation source and the second surface, based on the sensor signal.

The depth sensing location may be at a portion of a filter (or filter arrangement) which is configured to filter (for example, reduce the amount of a contaminant within) a fluid passing through the filter. The depth sensing location may be at a surface of a filter element which forms part of the filter, the filter element being configured to reduce the amount of a contaminant within a fluid passing through the filter.

The liquid may be contained in a vessel.

The liquid depth sensor may be configured to be located exterior to the vessel.

The vessel may be a portion of a pipeline. The pipeline may be a gas pipeline. The gas pipeline may carry natural gas or compressed air.

The vessel may be a portion of a filter which is configured to filter a fluid passing through it.

The liquid depth sensor may further comprise a window which is configured to be mounted to the vessel, the window being substantially transparent to the first and second detection amounts of radiation, the radiation source being configured such that, in use, the first and second amounts of detection radiation pass through the window.

The window may be formed from sapphire. The sapphire may be c-cut sapphire. The sapphire may be braised in place.

The liquid depth sensor may further comprise a heater, the heater being in thermal communication with said window and being configured to heat the window, the optical chemical analyser further comprising a thermal insulator which thermally isolates the heater from the vessel.

The liquid depth sensor may further comprise a vent passage, a first end of which is configured to be in fluid flow communication with a portion of the window which is in fluid flow communication with the fluid contained in the vessel and a second end which is in fluid flow communication with the exterior of the vessel; the vent passage further comprising a closing member, which in a normal, closed configuration substantially prevents fluid flow between the first and second ends of the vent passage, and which in an open configuration allows fluid flow between the first and second ends of the vent passage.

The second surface may be a surface of the vessel.

The liquid depth sensor may further comprise a first beam converging element configured to converge the first amount of radiation to a focus at a focus position which is substantially co-located with said liquid.

The liquid depth sensor may further comprise a beam expanding element configured to expand the first amount of radiation upstream of the first beam converging element.

The liquid depth sensor may further comprise a second beam converging element configured to converge the second amount of detection radiation to a focus at a focus position which is substantially co-located with said sensor arrangement.

The liquid depth sensor may further comprise a despeckling element, the radiation source being configured such that the first amount of detection radiation is incident on the despeckling element, and wherein the despeckling element is configured to reduce the effect of speckle within the first amount of radiation on the sensor signal.

The despeckling element may include a diffuser configured to rotate and arranged such that, in use, the first amount of detection radiation is incident thereon.

The liquid depth sensor may further comprises a reference channel, the reference channel comprising a second radiation source producing a fourth amount of detection radiation, the second radiation source being configured, in use, to direct the fourth amount of detection radiation so that it is incident on a reference surface; a second sensor arrangement arranged to receive a fifth amount of detection radiation, the fifth amount of detection radiation being a portion of the fourth amount of detection radiation which is reflected by the reference surface, the position at which the fifth amount of detection radiation is incident on the second sensor arrangement being dependent on a path length between the second radiation source and the reference surface, the second sensor arrangement further being configured to output a sensor signal indicative of the position at which the fifth amount of detection radiation is incident on the second sensor arrangement; and wherein the controller is configured to receive the sensor signal indicative of the position at which the fifth amount of detection radiation is incident on the second sensor arrangement and determine a measure indicative of the path length between the second radiation source and the reference surface based on the sensor signal indicative of the position at which the fifth amount of detection radiation is incident on the second sensor arrangement.

The second radiation source and radiation source producing the first amount of detection radiation may be one and the same.

The controller may be configured to calculate a corrected measure indicative of the depth of the liquid based on the sensor signal indicative of the position at which the second amount of detection radiation is incident on the sensor arrangement and the sensor signal indicative of the position at which the fifth amount of detection radiation is incident on the second sensor arrangement.

The liquid depth sensor may further comprise an imaging device.

The imaging device may be configured to produce an image of the depth sensing location.

The liquid depth sensor further comprising an imaging controller, the imaging controller being configured such that it selectively energises the imaging device based on the sensor signal.

The radiation source may be configured to direct the first amount of detection radiation through a volatile substance, the first amount of detection radiation transferring energy to the volatile substance, and wherein the radiation source is configured such that a total energy and/or a density of energy transferred to the volatile substance from the first amount of detection radiation is less than an ignition amount.

The liquid may comprise dust or powder, or the liquid may be instead a dust or powder.

An optical chemical analyser according to the first aspect of the invention or a liquid depth sensor according to a second aspect of the invention may further comprise an aerosol detection module, the aerosol detection module including a first intensity sensor configured to measure the intensity of an amount of radiation which is directed at a fluid before it is incident on the fluid, a second intensity sensor configured to measure the intensity of an amount of radiation which is which is backscattered by the fluid, and a processor configured to compare the intensity measured by the first intensity sensor and the intensity measured by the second intensity sensor to determine a measure indicative of the quantity of aerosol within the fluid.

The amount of radiation which is directed at the fluid may be the first amount of radiation. The amount of radiation which is directed at the fluid may be the first amount of detection radiation.

According to a third aspect of the invention there is provided a method of analysing a target using an optical chemical analyser, the optical chemical analyser comprising a radiation source; an optics module; a processor and a Spatial Interference Fourier Transform (SIFT) module including first and second dispersive elements and a detector; the method comprising the radiation source producing a first amount of radiation; the optics module directing the first amount of radiation such that it is incident on or directed through the target at a target location; the optics module receiving a second amount of radiation from the target; the optics module directing the second amount of radiation to the SIFT module; the SIFT module receiving the second amount of radiation; the first dispersive element receiving a first portion of the second amount of radiation; the second dispersive element receiving a second portion of the second amount of radiation; the first portion of the second amount of radiation received by the first dispersive element interfering with the second portion of the second amount of radiation received by the second dispersive element to form an interference pattern; the detector capturing an image of at least a portion of the interference pattern; the detector producing a detector signal based on the captured image; the processor receiving the detector signal from the detector; and the processor performing a Fourier transform on the detector signal to thereby obtain a frequency spectrum of the second amount of radiation.

The target may include a liquid species in a pipeline or vessel. The pipeline may be a gas pipeline. The gas pipeline may carry natural gas or compressed air.

The target may include a gas species in a pipeline or vessel. The pipeline may be a gas pipeline. The gas pipeline may carry natural gas or compressed air.

According to a fourth aspect of the invention there is provided a method of determining a measure indicative of the depth of the liquid using a liquid depth sensor suitable for use with a fluid pipeline, the liquid depth sensor comprising a radiation source; a sensor arrangement; and a controller; the method comprising the radiation source producing a first amount of detection radiation, the radiation source directing the first amount of detection radiation so that it is incident on a liquid at a depth sensing location; the sensor arrangement receiving a second amount of detection radiation, the second amount of detection radiation being a portion of the first amount of detection radiation which is reflected by the liquid, the position at which the second amount of detection radiation is incident on the sensor arrangement being dependent on a path length between the radiation source and a surface of the liquid; the sensor arrangement outputting a sensor signal indicative of the position at which the second amount of detection radiation is incident on the sensor arrangement; and the controller receiving the sensor signal and determining a measure indicative of the depth of the liquid based on the sensor signal.

According to a fifth aspect of the invention there is provided a spectrometer comprising an optical fibre, a first optical filter located at a first end of the optical fibre and a second optical filter located at the second end of the optical fibre, wherein the first optical filter is selected from the group consisting of an optical band pass filter, an optical band stop filter and an optical edge filter; and wherein the second optical filter is selected from the group consisting of an optical band pass filter, an optical band stop filter and an optical edge filter.

The first and second optical filters may both be edge filters. The first and second optical filters may both be long wave pass filters or may both be short wave pass filters.

The first and or second optical filter may be located adjacent their respective end of the optical fibre. In this case, radiation may not pass through another optical component when passing between the first optical filter and the first end of the optical filter. Likewise, radiation may not pass through another optical component when passing between the second optical filter and the second end of the optical filter.

The first and second optical filters may be configured to receive radiation and orientated such that an optical axis of each of the first and second optical filters is non-parallel with respect to an optical axis of the received radiation.

The spectrometer may be a Raman spectrometer including a radiation source which is configured to produce a first amount of Raman exciting radiation of a first wavelength that may excite Raman scattering in a sample, and the first and second optical filters may both be long wave pass filters which have a cut-off wavelength which is greater than the first wavelength.

According to a sixth aspect of the invention there is provided an optical arrangement for conveying radiation, the optical arrangement comprising an optical fibre, a first optical filter located at a first end of the optical fibre and a second optical filter located at the second end of the optical fibre, wherein the first optical filter is selected from the group consisting of an optical band pass filter, an optical band stop filter and an optical edge filter; and wherein the second optical filter is selected from the group consisting of an optical band pass filter, an optical band stop filter and an optical edge filter.

According to the sixth aspect the optical arrangement need not form part of a spectrometer, an may be used in any appropriate application, for example where it is desired to suppress any unwanted radiation florescence radiation produced by an optical fibre.

The first and or second optical filter may be located adjacent their respective end of the optical fibre. In this case, radiation may not pass through another optical component when passing between the first optical filter and the first end of the optical filter. Likewise, radiation may not pass through another optical component when passing between the second optical filter and the second end of the optical filter.

The first and second optical filters may be configured to receive radiation and orientated such that an optical axis of each of the first and second optical filters is non-parallel with respect to an optical axis of the received radiation.

The first and second optical filters may be configured to reduce an amount of florescent radiation which is transmitted by the optical arrangement. For example, in some embodiments said florescent radiation may be produced within the optical fibre.

According to a seventh aspect of the invention there is provided a connector assembly configured to couple with a fluid containing vessel, the connector assembly comprising a window which is configured to be substantially transparent to a portion of sensing radiation and to thereby allow the passage of the portion sensing radiation therethrough, a heater, the heater being in thermal communication with said window and being configured to heat the window, a vent passage, a first end of which is configured to be in fluid flow communication with a portion of the window which is in fluid flow communication with the fluid contained in the vessel and a second end which is configured to be in fluid flow communication with the exterior of the vessel; the vent passage further comprising a closing member, which in a normal, closed configuration substantially prevents fluid flow between the first and second ends of the vent passage, and which in an open configuration allows fluid flow between the first and second ends of the vent passage. The combination of heater and vent passage may act to substantially prevent undesired condensation from forming on the window. The heater can be used to raise the temperature of the widow and the vent can be used to purge relatively wet, hence condensation causing, gas from adjacent to the window.

The window may be formed from a material which is relatively thermally conductive, such that heat generated by the heater is conducted into the window.

The connector assembly may be configured such that the portion of sensing radiation passes through the window from a location interior to the vessel to a location exterior to the vessel. The connector assembly may also be configured such that a further portion of sensing radiation passes through the window from a location exterior to the vessel to a location interior to the vessel.

The sensing radiation may form part of a sensing apparatus. For example, the connector assembly may form part of a sensing arrangement, the sensing radiation being produced by and/or received by the sensing apparatus. The sensing apparatus may be a spectrometer or any other appropriate optical chemical analyser.

The connector assembly may further comprise a thermal insulator configured to thermally isolate the heater from the vessel to which the connector assembly is connected. The thermal insulator minimises the amount of heat which is conveyed from the heater to the vessel. This may help to minimise condensation which forms on the window.

The vessel may be a portion of a pressurised pipeline. The pipeline may be a gas pipeline. The gas pipeline may carry natural gas or compressed air.

The window may comprise sapphire, and optionally, the sapphire may be c-cut sapphire. It has been determined that sapphire, and in particular c-cut sapphire, has very low florescence characteristics. That is to say sapphire, and in particular c-cut sapphire, does not produce a significant amount of florescent radiation. Minimising florescent radiation may be beneficial in some applications, for example in applications in which the florescent radiation may be undesirable. One such example is if the radiation passing through the window is passing to an optical chemical analyser because fluorescent radiation may lead to the optical chemical analyser producing inaccurate results.

The connector assembly may be configured such that a normal to a surface of the window is non-parallel to a direction of propagation of the portion of sensing radiation, wherein the surface being a surface through which the portion of sensing radiation passes. This may help to prevent radiation which is reflected by the surface from travelling in a direction which is anti-parallel to the radiation which is incident on the surface.

According to an eighth aspect of the invention there is provided an optical chemical analyser comprising a target detection module, the target detection module being configured to detect a change in presence of a desired class of target and output a target change signal when a predetermined change in presence of the desired class of target is detected; and wherein the optical chemical analyser is configured such that at least a portion of the optical chemical analyser enters a powered-up state from a powered-down state based on the target change signal being output by the target detection module. This may prevent the portion of the optical chemical analyser from being power-up when it is unnecessary. This may extend the operating lifetime of the portion of the optical chemical analyser.

The at least a portion of the optical chemical analyser which enters a powered-up state from a powered-down state may be a detector and/or a source of radiation configured to be incident on a target in order for the optical analyser to output a signal as a function of a chemical composition of the target.

The target detection module may comprise a liquid depth sensor according to the second aspect of the present invention discussed above.

The controller of the liquid depth sensor may be configured to output the target change signal when the measure of the depth of the liquid exceeds a predetermined threshold.

BRIEF DESCRIPTION OF THE DRAWINGS

Specific embodiments of the present invention will now be described, by way of example only, with reference to the accompanying drawings, in which.

Equivalent features within the figures have been given the same numbering.

DETAILED DESCRIPTION

As previously discussed, the presence of contaminants within gas pipelines has been a problem for some time. In particular, the presence of liquid contaminants within gas pipelines may cause damage to gas equipment.

Known analysers for detecting the presence of contaminants within gas pipelines may not be capable of detecting liquid contaminants and in some cases may be rendered inoperative or require maintenance if they are exposed to liquid contaminants.

Figure 1:
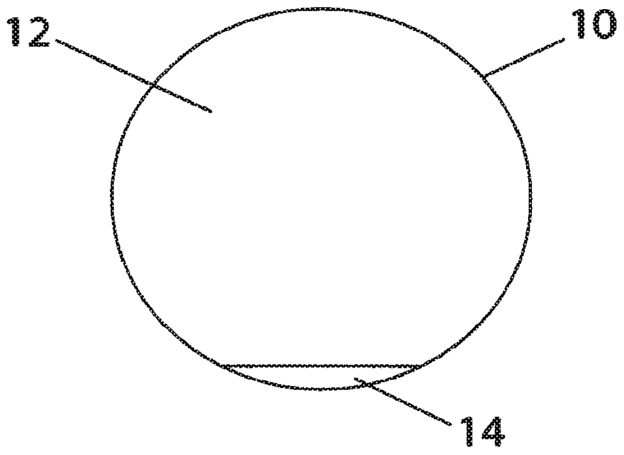
FIG. 1 shows a schematic cross-sectional view through a vessel in the form of a gas pipeline.

FIG. 1 shows a schematic cross-section of a gas pipeline 10 which may form part of a national transmission system (NTS) for conveying gas. The gas may be natural gas. The gas pipeline 10 includes a region containing gas 12 and a region which contains a liquid contaminant 14. The gas within the vessel (in this case the gas pipeline 10) is at an elevated pressure relative to atmospheric pressure. For example, the gas may have a pressure of above about 2 atmospheres. In some cases the gas may have a pressure of up to about 100 atmospheres. It can be seen that if a liquid contaminant 14 is present in the gas pipeline 10 the liquid contaminant collects at the lowest point of the gas pipeline 10 so as to form a pool of liquid contaminant.

Figure 2:
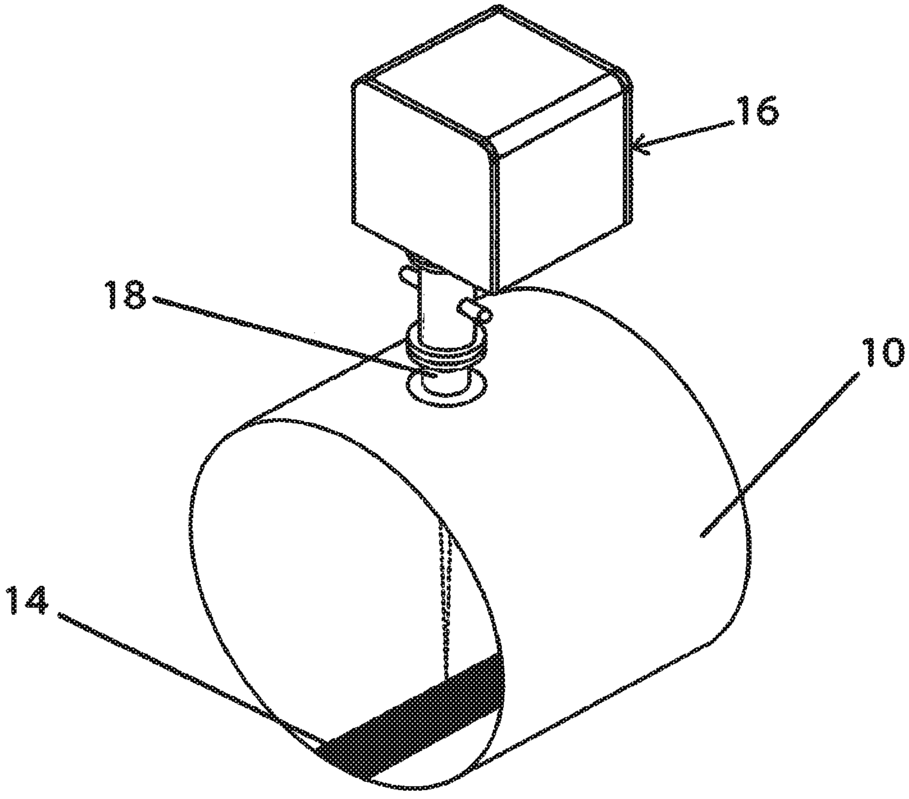
FIG. 2 shows a schematic perspective view of a portion of an embodiment of the present invention mounted to a vessel.

FIG. 2 shows a portion of an optical chemical analyser and a portion of a liquid depth sensor which are both contained within an on-pipe unit 16 which is mounted via a spur pipe 18 to the gas pipeline 10.

Figure 3:
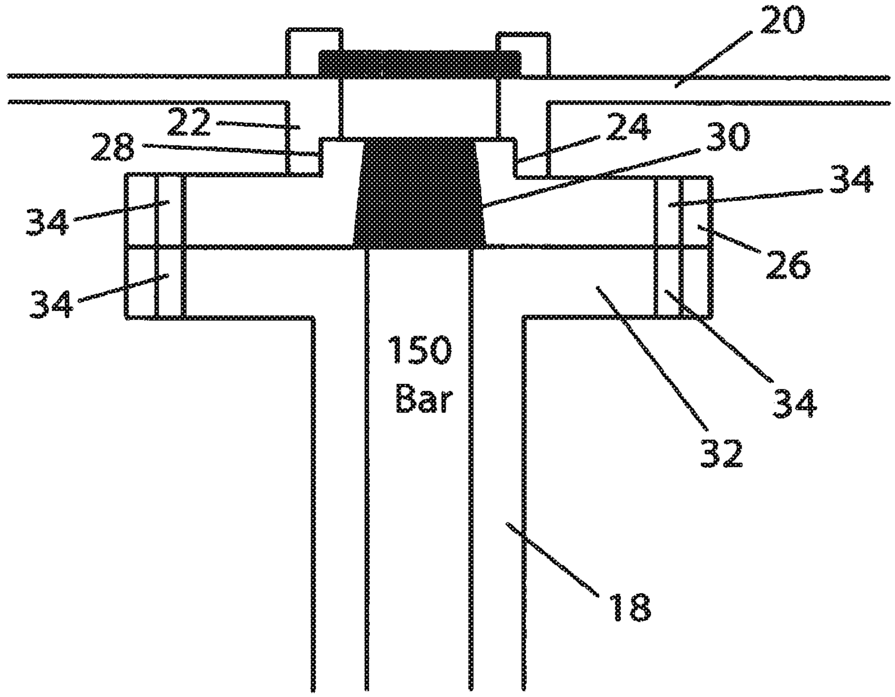
FIG. 3 shows a schematic cross-section through a portion of an embodiment of the present invention mounted to a spur pipe of a vessel.
Figure 4:
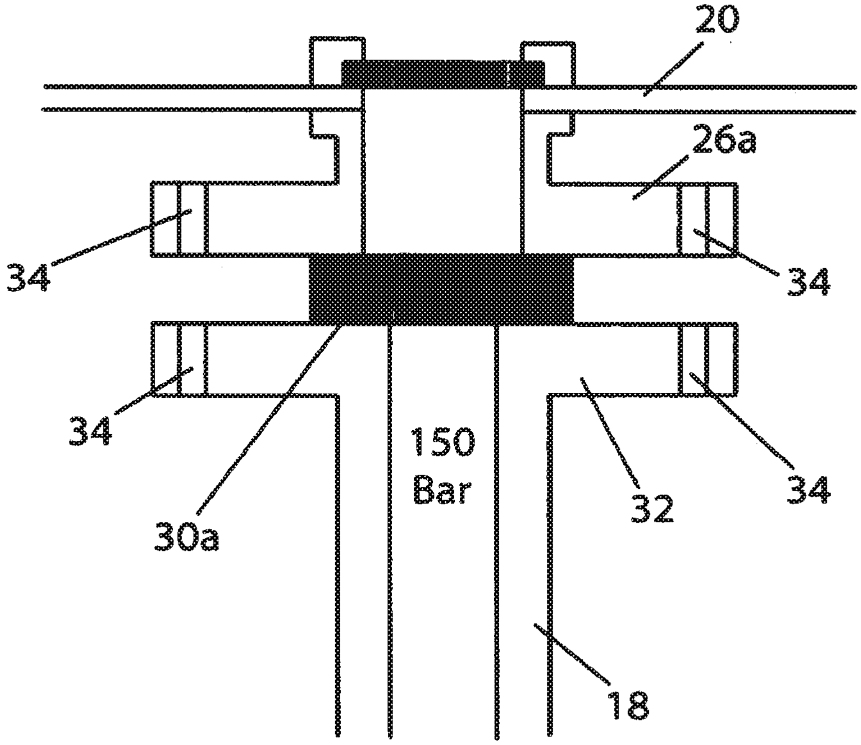
FIG. 4 shows a schematic cross-section through a portion of another embodiment of the present invention mounted to a spur pipe of a vessel.

FIGS. 3 and 4 show schematic cross-sectional views of two different arrangements which allow the on-pipe unit 16 to be mounted to the spur pipe 18 which is connected to the gas pipeline 10 (not shown in FIGS. 3 and 4).

Each embodiment shows a portion of casing 20 of the on-pipe unit 16.

In the embodiment shown in FIG. 3 the casing 20 includes a boss portion 22. The boss portion 22 includes a thread 24. A flange piece 26 is screwed to the boss portion 22 of the casing 20 via a thread 28 which corresponds with the thread 24 of the boss portion 22. The flange piece 26 includes a sight glass 30 which may also be referred to as a window. In this case the sight glass 30 is fused to the rest of the flange piece 26. Any appropriate material may be used for the sight glass 30 and the rest of the flange piece 26. In one embodiment, the sight glass 30 is formed from a borosilicate and the rest of the flange piece 26 is formed from a metal such as steel.

Fusing the sight glass 30 to the rest of the flange piece 26 ensures that there is substantially no gas leakage path between the sight glass 30 and the rest of the flange piece 26. The flange piece 26 is secured to a flange portion 32 of the spur pipe 18. The securing of the flange piece 26 to the flange portion 32 of the spur pipe 18 may be achieved in any conventional manner. For example, retainers such as bolts may be passed through apertures 34 in both the flange piece 26 and flange portion 32 of the spur pipe 18. The flange piece 26 is secured to the flange portion 32 of the spur pipe 18 such that there is substantially no gas leakage between the flange piece 26 and the spur pipe 18.

The embodiment shown in FIG. 4 differs from that shown in FIG. 3 in that the flange piece 26*a* is mounted to the casing 20 by welding (as opposed to a threaded connection as shown in FIG. 3). However, it will be appreciated that the flange piece 26*a* may be mounted to the casing 20 in any appropriate manner. For example, in some embodiments, the flange piece may be integral with the casing. In addition, instead of the flange piece 26*a* incorporating a sight glass which is fused to the flange piece (like that shown in FIG. 3), in the embodiment shown in FIG. 4 a sight glass 30*a* is sandwiched between the flange piece 26*a* and the flange portion 32 of the spur pipe 18. The sight glass 30*a* is sandwiched between the flange piece 26*a* and flange portion 32 such that there is substantially no gas leakage path between the sight glass 30*a* and the flange piece 26*a*, and such that there is substantially no gas leakage path between the sight glass 30*a* and flange portion 32 of the spur pipe 18. The sight glass 30*a* may be made from any appropriate material. In one example, the sight glass 30*a* is formed from sapphire.

Sapphire may be used as the material for a sight glass/window in any embodiment of liquid depth sensor and/or optical chemical analyser. The sapphire may be c-cut sapphire. The sight glass/window may be held in place (e.g. secured to the flange piece) by any appropriate method including gluing or braising.

In some embodiments it is preferred to select the material from which the sight glass 30, 30*a* is formed based on its electromagnetic transmission characteristics and fluorescence characteristics. It may be beneficial for the sight glass to allow electromagnetic radiation of a desired wavelength or range of wavelengths to pass through it substantially unattenuated. In addition, it may be desirable for the sight glass to exhibit minimal fluorescence at a particular wavelength or range of wavelengths such that any fluorescent radiation does not affect measured radiation which passes through the sight glass.

The spur pipe to which the on-pipe unit is attached may be a spur pipe which is already connected to the gas pipeline. Alternatively, a spur pipe may be connected to the gas pipeline using any appropriate method. For example, the spur pipe may be hot tapped to the gas pipeline as is well-known in the art.

It will be appreciated that in other embodiments a portion of the optical chemical analyser and/or liquid depth sensor may be mounted to a vessel (e.g. a gas pipeline) in any appropriate manner.

Figure 5:
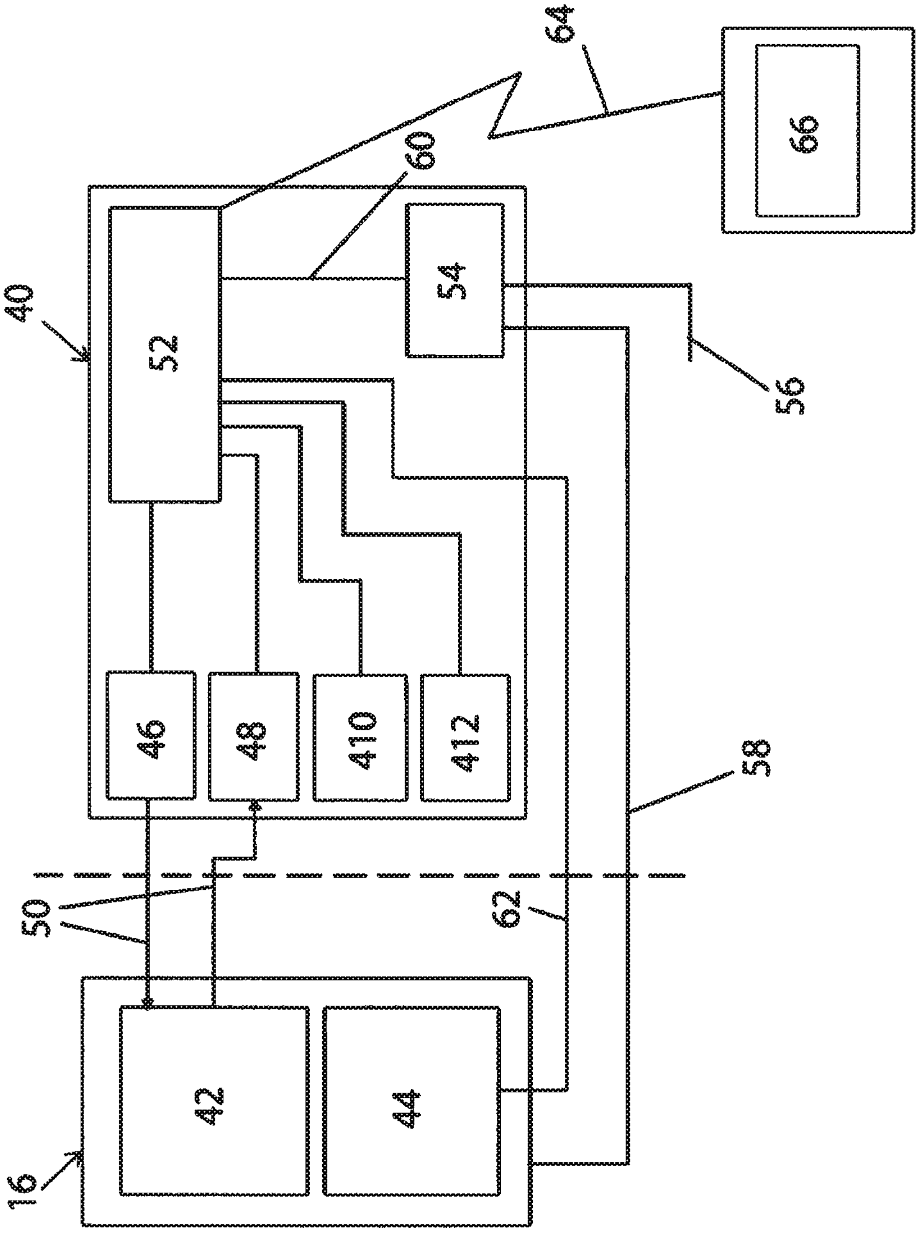
FIG. 5 shows a schematic view of an embodiment of the invention.

FIG. 5 shows a schematic representation of an optical chemical analyser and liquid depth sensor in accordance with an embodiment of the present invention. The optical chemical analyser and liquid depth sensor includes an on-pipe unit 16 (as previous discussed) and an off-pipe unit 40.

In this embodiment, the on-pipe unit 16 includes various optics which form part of the optical chemical analyser and which are represented schematically by box 42. The on-pipe unit 16 also includes components of the liquid depth sensor which are illustrated schematically by box 44.

In this embodiment the off-pipe unit 40 includes a source 46 of a first amount of radiation which forms part of the optical chemical analyser. The off-pipe unit 40 also includes a detector 48 which forms part of the optical chemical analyser. The source 46 of the first amount of radiation and the detector 48 are optically linked to components of the optical chemical analyser 42 which form part of the off-pipe unit 16 by at least one optical fibre. In this case, the radiation source 46 and detector 48 are optically linked to the components 42 of the optical chemical analyser which form part of the off-pipe unit 16 by a pair of optical fibres represented by the two arrows 50 within the Figure. In some embodiments the radiation source 46 and detector 48 may be optically linked to the components 42 of the optical chemical analyser which form part of the off-pipe unit 16 by at least one optical fibre. In the shown embodiment the radiation source 46 and detector 48 are optically linked to the components 42 of the optical chemical analyser which form part of the off-pipe unit 16 by two optical fibres: a first optical fibre carries radiation produced by the radiation source to the off-pipe unit, and a second optical fibre carries radiation from the gas pipeline, via the components 42 of the optical chemical analyser which form part of the off-pipe unit 16, to the detector.

The radiation source 46 and detector 48 are also linked to a microprocessor 52. Any appropriate microprocessor may be used. The microprocessor may be capable of carrying out processing operations and/or controller operations. The microprocessor 52 is also connected to the components of the liquid depth sensor 44 located in the off-pipe unit 16 via connection 62. Any appropriate connection may be used to link components to the microprocessor. For example, the connection may include a USB connection.

The off-pipe unit 40 also includes a power supply unit (PSU) 54. The PSU 54 receives power via power line 56 and distributes power to components within the on-pipe unit 16 and off-pipe unit 40 via connections 58 and 60 respectively. In alternative embodiments each of the on-pipe unit and off-pipe units may be supplied separately with power.

In the embodiment shown in FIG. 5 the microcontroller 52 is connected via connection 64 to a remote terminal 66. In some embodiments the connection 64 may be an ethernet-type connection, although any appropriate connection may be used. The remote terminal may be a personal computer. The connection 64 between the remote terminal 66 and microprocessor 52 enables the remote terminal to retrieve data from the microprocessor 52 and/or to remotely control an aspect of the operation of the microprocessor 52. For example, the connection 64 may enable the remote terminal 66 to monitor data produced by the optical chemical analyser as to the presence or otherwise of particular chemicals within a target; and/or to monitor data produced by the liquid depth sensor which indicates the depth of a liquid at a target location.

The operation of the various components of the optical chemical analyser and liquid depth sensor referred to above is discussed in more detail below.

Figure 6:
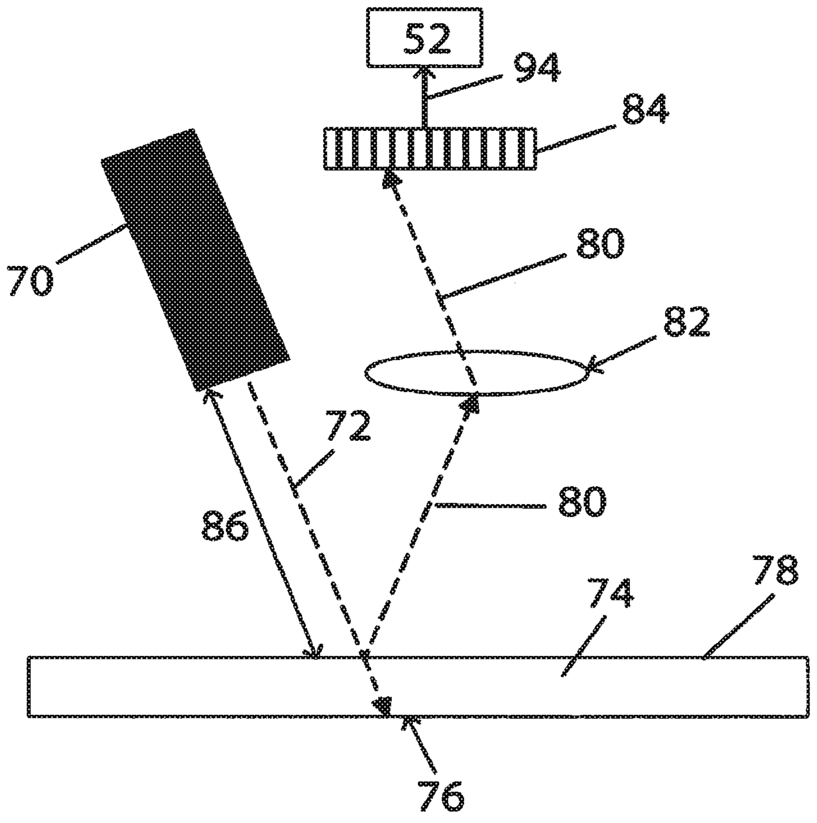
FIG. 6 shows a schematic view of a portion of a liquid depth sensor in accordance with an embodiment of the present invention.

FIG. 6 shows a schematic representation of a liquid depth sensor which may form part of an embodiment of the invention. The liquid depth sensor includes a radiation source 70. The radiation source 70 produces a first amount of detection radiation 72. In one example the radiation source may be a diode laser with a power output of 10 mW and the first amount of detection radiation may be electromagnetic radiation which has a wavelength of 633 nm. The radiation source is configured, in use, to direct the first amount of detection radiation 72 so that it is incident on a liquid 74 at a liquid depth sensing location 76. The radiation source 70 may be any appropriate source of radiation, for example, any appropriate type of laser.

In some embodiments the liquid 74 is contained in a vessel, for example a portion of a pipeline, and the liquid depth sensor is located exterior to the vessel (for example exterior to a portion of a pipeline). For example, a portion of the liquid depth sensor may be located, as shown in FIG. 2, in an on-pipe unit 16 which is mounted to a gas pipeline 10 via a spur pipe 18 and a portion of the liquid depth sensor may be located in an off-pipe unit. In the embodiment shown, the first amount of detection radiation 72 produced by the radiation source 70 passes through a window (such as those shown in FIGS. 3 and 4) so as to pass from the exterior of the vessel (for example the on-pipe unit 16) into the vessel (e.g. pipeline 10) via the window.

In a normal operating state of the vessel (e.g. gas pipeline) there is substantially no liquid in the vessel. In a liquid present state of the vessel, liquid, for example at least one liquid contaminant may be present within the vessel, for example at the bottom of a gas pipeline as shown in FIG. 6.

A portion of the first amount of detection radiation 72 is reflected by the liquid 74 (in this case a surface 78 of the liquid 74). The portion of the first amount of detection radiation which is reflected by the liquid 74 may be referred to as a second amount of detection radiation. The second amount of detection radiation is indicated by the arrow 80. The second amount of radiation passes through various optics indicated schematically by 82 and is incident on a sensor arrangement 84 which is arranged to receive the second amount of detection radiation 80.

In some embodiments the sensor arrangement may include a CCD or CMOS-type detector. In some embodiments the pitch (i.e. distance between adjacent pixels of the sensor) may be approximately 3 μm to 5 μm. An example of a suitable CCD is a CCD with a pitch of 5 μm and dimensions of 1280 by 1024 pixels.

The position at which the second amount of detection radiation 80 is incident on the sensor arrangement 84 is dependent upon a path length 86 between the radiation source 70 and the surface 78 of the liquid 74. The position at which the second amount of detection radiation 80 is incident on the sensor arrangement 84 is also dependent upon a path length between the sensor arrangement 84 and the surface 78 of the liquid 74. Consequently, the position at which the second amount of detection radiation is incident on the sensor arrangement is dependent upon the depth of the liquid at the depth sensing location. This is discussed in more detail with reference to FIG. 7.

Figure 7:
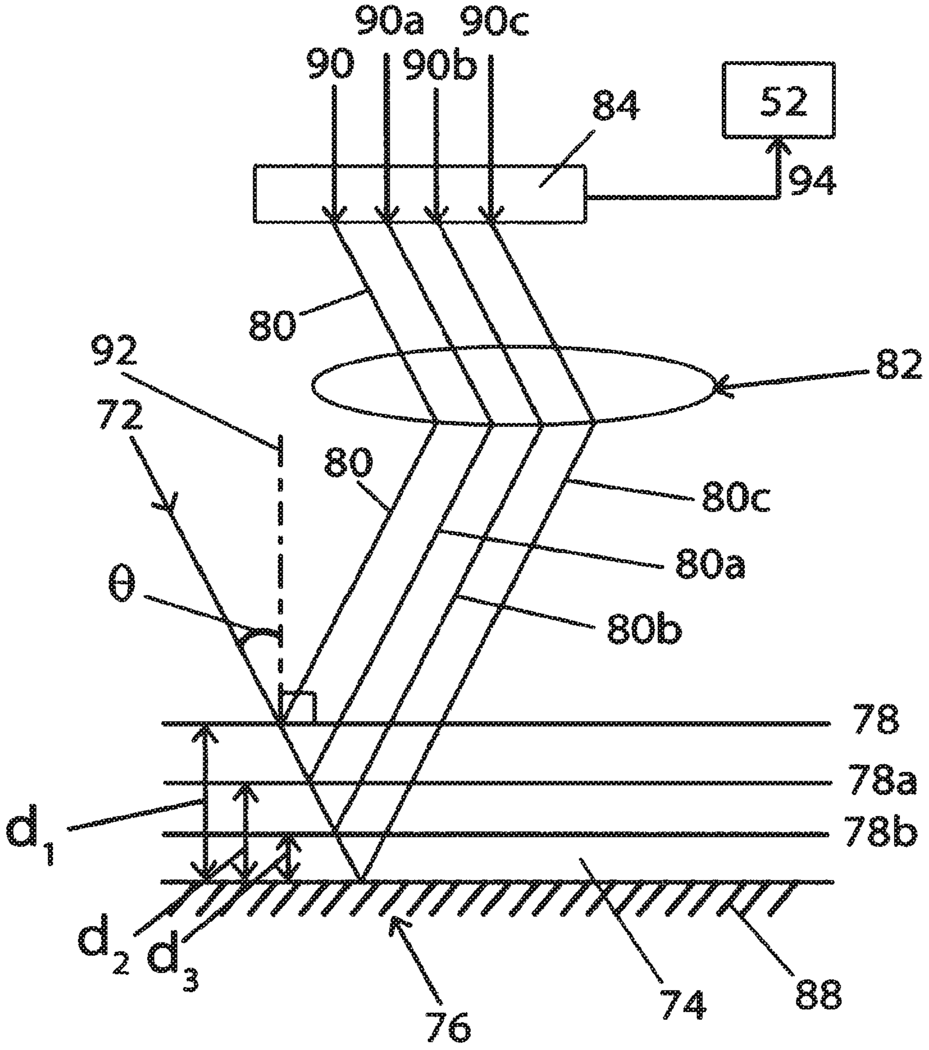
FIG. 7 shows a schematic view of a portion of the liquid depth sensor shown in FIG. 6, wherein a liquid is shown having several different depths.

FIG. 7 shows a schematic view of a portion of a vessel 88. As previously discussed the vessel 88 may support a liquid, for example a liquid contaminant when the vessel is in a liquid present state. The three different potential surfaces of the liquid are shown within the Figure. These are marked as 78, 78*a* and 78*b*. The depth of the liquid when the liquid has a surface indicated by 78, 78*a* or 78*b* is marked on the Figure as $d_1$, $d_2$ and $d_3$ respectively. Depending on whether the surface of the liquid is that indicated by 78, 78*a* or 78*b*, the path of the second amount of detection radiation which is reflected by the surface of the liquid will be different. The different paths of the second amount of detection radiation if the first amount of detection radiation is reflected by surface 78, 78*a* or 78*b* are indicated as 80, 80*a* and 80*b* respectively. In addition, the path of a second amount of detection radiation which is reflected by the surface of the vessel 88 is indicated by 80*c*.

The paths of the second amount of detection radiation 80, 80*a*, 80*b* and 80*c* are then directed by the optics 82 and are incident on the sensor arrangement 84. The positions at which the second amounts of radiation 80, 80*a*, 80*b* and 80*c* are incident on the sensor arrangement 84 are indicated by 90, 90*a*, 90*b* and 90*c* respectively. Hence, it can be seen that the position at which the second amount of detection radiation is incident on the sensor arrangement 84 is dependent on the depth of the liquid. It follows that the position at which the second amount of detection radiation is incident on the sensor arrangement is dependent upon the path length between the radiation source and the surface of the liquid, and also upon the path length between the sensor arrangement and the surface of the liquid. This is because the path length between the radiation source or the sensor arrangement and the surface of the liquid is dependent upon the depth of the liquid.

For example, with reference to FIG. 7, a change in the depth d of the liquid will result in a change in path length l between the radiation source and the surface of the liquid which is given by the formula $$l = \frac{d}{\cos\theta} \quad (1)$$

where θ is the angle subtended between the path of the first amount of detection radiation 72 and a normal 92 to the surface of the liquid.

The sensor arrangement 84 may further be configured to output a sensor signal (shown schematically as 94) which is indicative of the position at which the second amount of detection radiation is incident on the sensor arrangement. The liquid depth sensor may further include a microprocessor 52 which is configured to receive the sensor signal 94 and determine a measure indicative of the depth of the liquid based on the sensor signal 94.

In some embodiments the liquid depth sensor may be calibrated. The liquid depth sensor may be calibrated in any appropriate way. For example, the first amount of detection radiation 72 produced by the radiation source 70 may be directed at the depth sensing location 76 when substantially no liquid is present at the depth sensing location 76. In this case, the first amount of detection radiation will be reflected by the surface of the vessel 88 at the depth sensing location. With reference to FIG. 7, the portion of the first amount of detection radiation 72 which is reflected by the surface of the vessel 88 will travel along path 80*c* and be incident upon the sensor arrangement at position 90*c*.

The sensor arrangement 84 outputs sensor signal 94 which is indicative of the position 90*c* at which the radiation is incident on the sensor arrangement. The sensor signal is supplied to the microprocessor 52 and the controller may store this sensor signal as being indicative of the presence of no liquid within the vessel 88 at the depth sensing location 76.

Subsequently, if liquid (for example a liquid contaminant) becomes located at the depth sensing location 76, then the position of the second amount of detection radiation received by the sensor arrangement 84 will change from the position of the radiation reflected by the surface of the vessel. This will result in a change in the sensor signal output by the sensor arrangement. The controller may determine that a change in the received sensor signal from the calibrated stored sensor signal (when the first amount of detection radiation is reflected by the surface of the vessel), is indicative of liquid (of a particular depth) being present at the depth sensing location 76.

In some embodiments the liquid depth sensor may be configured such that the controller outputs a signal which only indicates the presence (or otherwise) of liquid at the depth sensing location. In other embodiments the liquid depth sensor may be configured such that it can determine a measure indicative of the actual depth of the liquid at the liquid sensing location. In both of these examples the controller determines a measure indicative of the depth of a liquid based on the sensor signal. In the embodiment in which the controller determines the presence or otherwise of a liquid at the depth sensing location, the controller either determines that the depth of the liquid is substantially zero (i.e. no liquid is present at the depth sensing location) or determines that the depth of the liquid is non-zero (i.e. that liquid is present at the depth sensing location). Whereas the other embodiment may include a controller which is capable of determining a measure of the actual depth of the liquid at the depth sensing location.

In some embodiments, as previously discussed, the controller determines a measure indicative of the depth of the liquid at the depth sensing location based on the sensor signal output by the sensor arrangement, which depends upon the position at which the second amount of detection radiation is received by the sensor arrangement. In some embodiments the controller determines the position that the second amount of detection radiation is incident on the sensor arrangement using peak fitting algorithms to determine the centre point of the image second amount of radiation which is incident on the sensor arrangement. For example, in the case where the sensor arrangement includes a CCD, the controller may monitor the amount of the second amount of radiation which is incident on each pixel of the CCD and then apply peak fitting algorithms, which are well known to a person skilled in the art, to determine the position of the centre of the second amount of radiation which is incident on the CCD based on the amount of the second amount of radiation which is incident on each pixel.

Figure 8:
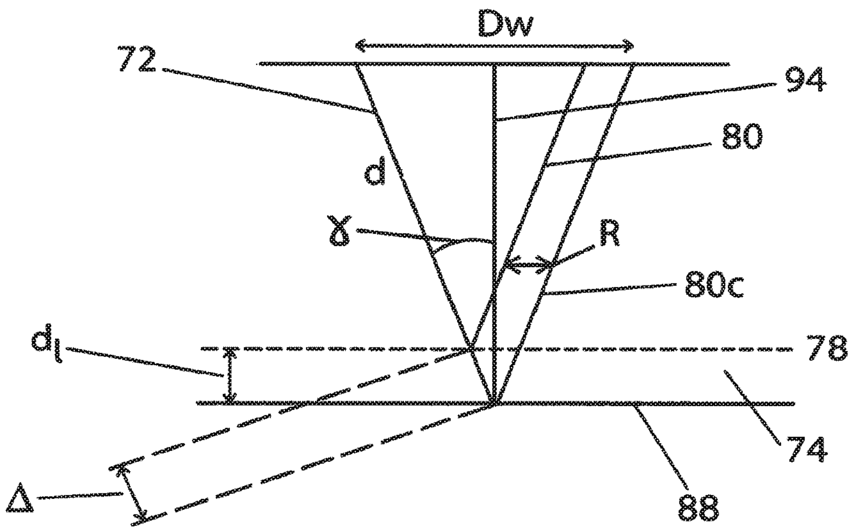
FIG. 8 shows a schematic view of a portion of the liquid depth sensor shown in FIGS. 6 and 7.

Referring to FIG. 8, in a particular embodiment in which a liquid depth sensor is mounted to a vessel in the form of a pipeline (as shown in FIG. 2) the distance d between the window between the on-pipe unit and the depth sensing location at the bottom of the gas pipeline may be about 1.8 m. The diameter of the window in this embodiment may be about 76 mm.

The maximum angle which can be subtended between the first amount of detection radiation 72 and the a normal 94 to the surface 78 of a liquid 74 is defined as γ. Angle γ is the maximum angle which the first amount of detection radiation 72 can subtend with the normal 94 to the surface of the vessel 88 whilst the first amount of detection radiation can be directed from the radiation source through the window to the depth sensing location and the second amount of radiation which is reflected from the surface of the vessel 88 can pass through the window and be received by the sensor arrangement. If the width of the window is $D_W$ the maximum angle γ is given by $$\gamma \approx \frac{D_W}{2d} \qquad (2)$$

where γ is in radians.

If it is desired to detect a depth of liquid $d_l$ equal to 0.1 mm, then the change in path length Δ of the first amount of detection radiation before it is reflected will be given by $$\Delta = \frac{d_l}{\cos\gamma} = \frac{0.1\text{ mm}}{\cos(0.021)} = 0.10002\text{ mm} \qquad (3)$$

Consequently the displacement R (which is shown horizontally within the Figure) between the amount of detection radiation 80*c* reflected by the vessel 88 and the second amount of detection radiation 80 reflected by the surface 78 of the liquid 74 is given by the following formula $$R=2\sqrt{\Delta 2-d_l^2}=2\sqrt{0.10002\text{mm}^2-0.1\text{mm}^2}=0.0042\text{ mm} \qquad (4)$$

The displacement R due to a liquid depth $d_l$ of 0.1 mm is 0.0042 mm and if the pitch of the detector used to measure said displacement is 5 μm then, in order for the detector (in this case CCD) to measure the displacement R, it may be desirable to magnify the displacement such that the displacement is equivalent to approximately 2 pixels of movement at the detector. In this case, due to the fact that the pitch of the detector is 5 μm, 2 pixels of movement will be equal to 10 μm of movement.

Consequently, in order for the displacement R of 0.42 μm to produce a displacement at the sensor arrangement of approximately 10 μm, a magnification of approximately 2.5 will be required.

Figure 9:
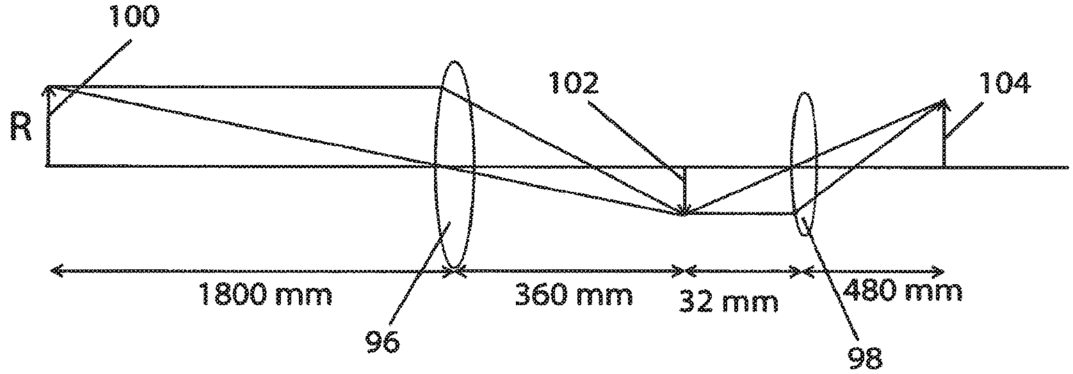
FIG. 9 shows a schematic view of a lens arrangement which may form part of the liquid depth sensor shown in FIGS. 6 to 8.

Optics 82 which are located along the path of the second amount of detection radiation upstream of the sensor arrangement 84 may be configured to produce the desired magnification of approximately 2.5. FIG. 9 shows a schematic view of an optical system which may form part of the optics 82 in the path of the second amount of detection radiation upstream of the sensor arrangement 84 in order to produce suitable magnification.

The optical arrangement shown in FIG. 9 includes an objective lens 96 and an imaging lens 98. The focal length of the objective lens is 300 mm and the focal length of the imaging lens is 30 mm. Within the optical system there is an object 100 which corresponds to the displacement R and which has a value in this example of 4.2 μm. The distance between the objective lens 96 and the object (which in this case is the displacement R located at the depth sensing location at the bottom of the vessel 88) is approximately 1800 mm. This is due to the fact that the objective lens 96 will be located within the on-pipe unit. If the objective lens 96 and imaging lens 98 are spaced by a total distance of 392 mm, then an intermediate image 102 will be formed between the object lens 96 and imaging lens 98 at a location 360 mm from the object lens. In this case the intermediate image 102 will have a height of 0.84 μm.

As can be seen in the Figure a final image 104 is formed at the opposite side of the image lens 98 to the intermediate image 102. The final image 104 is spaced from the image lens 98 by a distance of 480 mm. The final image 104 has a height 12.6 μm.

The magnification of the optical system shown in FIG. 9 is given by the height of the final image 104 divided by the height of the object 100 (i.e. displacement R), which in this case is 12.6 μm divided by 4.2 μm, which is equal to 3 (i.e. sufficiently close to the desired magnification of approximately 2.5). It will be appreciated that any appropriate optical system may be used to create any desired magnification of the displacement R such that a displacement R due to a desired change in depth of liquid can be measured by a sensor arrangement having a given resolution (e.g. pitch or pixel spacing).

In some embodiments, in order to improve the accuracy of the liquid depth sensor it may be desirable to minimise the diameter of the first amount of detection radiation when it is incident on the liquid at the bottom of the vessel. By reducing the diameter of the first amount of detection radiation when it is incident on the liquid, this will reduce the diameter of the second amount of radiation when it is incident on the sensor arrangement, thereby making it easier for the sensor arrangement to detect the position of the second amount of detection radiation and thereby allow the controller to determine a more accurate measure indicative of the depth of the liquid based on the sensor signal produced by the sensor arrangement.

In some embodiments, in order to improve the accuracy of the liquid depth sensor it may be desirable to maximise the diameter of the first amount of detection radiation when it is incident on the liquid at the bottom of the vessel. Maximising the diameter of the first amount of radiation may be beneficial in some applications. For example, if the fluid through which the first amount of detection radiation passes (or the liquid upon which the first amount of detection radiation is incident) fluoresces in the presence of the first amount of detection radiation, it may be advantageous to maximise the diameter of the first amount of detection radiation so that the power density of the first amount of radiation is reduced, thereby reducing fluorescence caused by the first amount of detection radiation. Reducing the amount of fluorescence may be advantageous because the fluorescent radiation may adversely affect the performance of the liquid depth sensor and/or optical chemical analyser.

In other embodiments, the first amount of detection radiation may comprise a plurality of discrete portions (e.g. spots) of radiation which is incident on the liquid at the bottom of the vessel. In other embodiments, the first amount of detection radiation may have any appropriate configuration. For example, in some embodiments, the first amount of radiation may form a generally linear shape such as a line which is incident on the liquid at the bottom of the vessel.

In the absence of any additional optics, the diameter of the first amount of detection radiation when it is incident on the liquid within the vessel will be governed by the divergence of the source of the first amount of detection radiation and the path length between the source of the first amount of detection radiation and the liquid.

Figure 10:
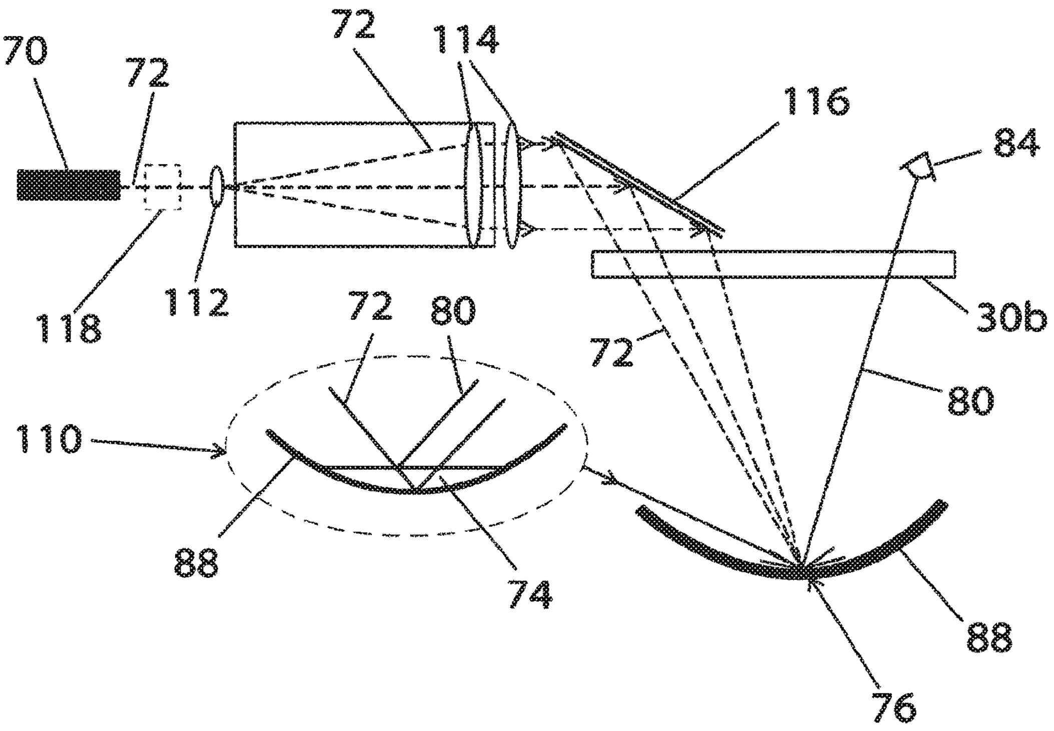
FIG. 10 shows a schematic view of a portion of the liquid depth sensor shown in FIGS. 6 to 9.

FIG. 10 shows a schematic illustration of an embodiment of a liquid depth sensor which is configured to reduce the diameter of the first amount of detection radiation 72 when it is incident on the liquid 74 at the depth sensing location 76 within the vessel 88. In order to aid clarity, FIG. 10 shows an enlargement indicated by 110 of the vessel 88.

As previously discussed, it can be seen that a radiation source 70 produces a first amount of detection radiation 72 which is directed such that it is incident on a liquid 74 at the bottom of a vessel 88 such that a second amount of detection radiation 80 is reflected by the liquid 74 at the bottom of the vessel 88. The second amount of detection radiation 80 is then received by a sensor arrangement 84. As previously discussed, both the first amount of detection radiation 72 and second amount of detection radiation 80 pass through a substantially transparent window 30*b* which is mounted to the vessel 88. As previously discussed, the window 30*b* is mounted to the vessel such that the window is substantially gas tight and hence leakage of any gas contained within the vessel 88 between the vessel and the window is substantially prevented. The window 30*b* may be mounted to the vessel 88 in any appropriate manner such as those shown in FIGS. 3 and 4.

The liquid depth sensor includes a beam expanding element 112 which is configured to expand the first amount of detection radiation 72. The liquid depth sensor also includes first and second beam converging elements 114 which are collectively configured to converge the first amount of detection radiation to a focus at a focus position which is substantially co-located with the liquid 74.

Although the embodiment shown has two beam converging elements 114, other embodiments may have any appropriate number of beam converging elements, for example, in some embodiments there may only be one beam converging element. Some embodiments may not include such a beam converging element. It will be noted that the beam converging elements 114 are located downstream of the beam expanding element 112. That is to say, the beam expanding element 112 is located upstream (having regard to the first amount of detection radiation 72) of the beam converging elements 114.

The liquid depth sensor shown in FIG. 10 also includes a beam directing element which directs the first amount of detection radiation towards the depth sensing location 76. In this embodiment the radiation directing element 116 is a reflective element (e.g. a mirror). It will be appreciated that in other embodiments the radiation directing element may be any appropriate radiation directing element which is capable of directing the first amount of detection radiation 72. Furthermore, in other embodiments, the liquid depth sensor may include any appropriate number of radiation directing elements along the path of the first and/or second amounts of detection radiation.

In some embodiments it may be desirable to include a beam converging element (not shown) which is located in the path of the second amount of detection radiation and is configured to converge the second amount of detection radiation to a focus at a focus position which is substantially co-located with the sensor arrangement. This may help to reduce the diameter of the second amount of detection radiation when it is incident on the sensing apparatus and thereby increase the accuracy of determining the position at which the second amount of detection radiation is incident on the sensing apparatus and hence increase the accuracy of the determination by the controller of the measure indicative of the depth of the liquid based on the sensor signal produced by the sensor arrangement.

The liquid depth sensor also includes a despeckling element 118. The despeckling element is located in the path of the first amount of detection radiation 72. The first amount of detection radiation 72 is incident on the despeckling element 118. The despeckling element is configured to reduce the effect of speckle within the first amount of detection radiation 72 on the sensor signal produced by the sensor arrangement 84.

Speckle is a well-known effect within the radiation produced by coherent radiation sources (e.g. lasers). Speckle pattern results from the interference of coherent radiation which is scattered from a rough surface (such as the surface of a liquid). It has been found that the speckle pattern within the second amount of detection radiation 80 which is reflected by the surface of the liquid 74 can fluctuate over time thus changing the shape of the second amount of detection radiation 80 which is measured by the sensing arrangement 84. The change in shape of the second amount of detection radiation measured by the sensing arrangement 84 may cause the sensing arrangement to incorrectly determine that a movement of the position at which the second amount of detection radiation is incident on the sensor arrangement (and hence a change in depth of the liquid) has occurred.

Consequently, the inventors have found that the use of a despeckling element in order to reduce the amount of speckle in the second amount of detection radiation improves the determination by the sensor arrangement of the location at which the second amount of detection radiation is incident on the sensor arrangement, and consequently improves the measure indicative of the depth of the liquid determined by the controller.

In one embodiment the despeckling element may take the form of a diffuser plate which is mounted in the path of the first amount of detection radiation such that the first amount of detection radiation is incident thereon and passes therethrough. The diffuser plate may take any appropriate form (for example the diffuser plate may take the form of frosted glass). The diffuser plate is rotated by a motor such that the portion of the diffuser plate through which the first amount of detection radiation passes varies with time. It follows that the first amount of radiation passes through a rough surface of the diffuser plate which varies over time. Consequently, the rotating diffuser smoothes and thereby minimises the speckle pattern.

It will be appreciated that, in other embodiments, any appropriate despeckling element may be used. For example, oscillating mirrors or passing the first amount of detection radiation through a vibrating fibre optic may be used as will be well understood by a person skilled in the art.

Some embodiments of liquid depth sensor may be configured such that the sensor arrangement is arranged to receive a third amount of detection radiation, wherein the third amount of detection radiation is a portion of the first amount of detection radiation which is reflected by a second surface in a similar manner to the way in which the second amount of detection radiation is reflected by a surface of the liquid. The position at which the third amount of detection radiation is incident on the sensor arrangement is dependent on a path length between the radiation source and the second surface (and also dependent on a path length between the sensor assembly and the second surface). The sensor arrangement may further be configured to output a sensor signal indicative of the position at which the third amount of detection radiation is incident on the sensor arrangement.

This concept is explained in more detail with reference to FIG. 7. The figure shows an amount of liquid 74 within the vessel 88 such that the surface 78 is the surface of the liquid 74. Consequently the surfaces indicated by 78*a* and 78*b* within the figure are irrelevant to the discussion of this concept. As previously discussed, it can be seen that the first amount of detection radiation 72 is incident on the surface 78 of the liquid 74 and is reflected by the surface 78 of the liquid 74. The reflected portion of the first amount of detection radiation 72 forms a second amount of detection radiation 80 which is then incident on the sensor arrangement 84 at the position 90.

In addition, if the liquid 74 is at least partially transparent to the first amount of detection radiation 72 then, a portion of the first amount of detection radiation 72 which is not reflected by the surface 78 of the liquid 74 will travel through the liquid 74 and be incident upon a second surface, in this case the surface of the vessel 88. The portion of radiation which is reflected by the surface of the vessel 88 may be referred to as a third amount of detection radiation and is indicated by 80*c* within FIG. 7. The third amount of detection radiation 80*c* is incident on the sensor arrangement 84 at the position 90*c*. As previously discussed, the distance between the locations 90 and 90*c* (i.e. the positions at which the second amount of detection radiation and third amount of detection radiation respectively or incident upon the sensor arrangement 84) is dependent upon the difference in path length of the first amount of detection radiation 72 between where it is reflected by the surface 78 of the liquid 74 and where it is reflected by the surface of the vessel 88.

In the case shown in FIG. 7, the distance between the position at which the first amount of detection radiation is reflected by surface 78 and the position at which the first amount of detection radiation is reflected by the surface of the vessel 88 is given by equation 1, where d is equal to $d_1$. Again, as previously discussed, the distance between the point at which the first amount of detection radiation is reflected by the surface 78 of the liquid and the point at which the first amount of detection radiation 72 is reflected by the surface of the vessel 88 is of course dependent on the depth of the liquid 74, which in this case is $d_1$.

It follows that the controller may be configured to determine a measure indicative of the difference between the path length between the radiation source and the surface 78 of the liquid 74, and the path length between the radiation source and the second surface (in this case the surface of the vessel 88), based on the sensor signal produced by the sensor arrangement. It follows that the controller, based on the sensor signal produced by the sensor arrangement, may be configured to determine a measure indicative of the path length of between where the first amount of detection radiation is reflected by the surface of the liquid 78 and where the first amount of detection radiation is reflected by the second surface (in this case the surface of the vessel 88).

In other words, the controller may be configured to measure a distance between the location 90 at which the second amount of detection radiation is incident on the sensor arrangement 84 and the location 90*c* at which the third amount of detection radiation 80*c* is incident on the sensor arrangement 84 in order to determine a measure indicative of the distance between the surface 78 of the liquid 74 and the surface of the vessel 88. The distance between the surface 78 of the liquid 74 and the second surface (in this case the surface of the vessel 88) may be the depth of the liquid 74.

Determining the depth of the liquid at the depth sensing location in this manner may be advantageous for several reasons. For example, changes in characteristic of the first amount of detection radiation will affect the second amount of detection radiation and third amount of detection radiation in an equivalent manner. For example, if the direction of the first amount of detection radiation produced by the radiation source changes then this will affect both the position at which the second amount of detection radiation is incident upon the sensor arrangement and the position at which the third amount of detection radiation is incident upon the sensor arrangement. In some embodiments, the distance between the positions 90 and 90*c* will be affected less by a change in direction of the first amount of detection radiation than the absolute movement of positions 90 and 90*c* caused by the change in direction of the first amount of detection radiation. Consequently, if the controller calculates the depth of the liquid based on the difference between the position 90 and the position 90*c* then any error caused by the change in direction of the first amount of detection radiation in determining the measure indicative of the depth of the liquid will be minimised.

Another potential advantage is that, unlike embodiments in which only the second amount of detection radiation which is reflected by the surface of the liquid is measured in order to determine a measure indicative of the depth of the liquid, no initial calibration in order to determine the position at which a portion of the first amount of the radiation which is reflected by a surface of the vessel is required. This is because in a situation whereby the sensor arrangement 84 measures the position of the incident second amount of detection radiation and third amount of detection radiation simultaneously, the controller is continually provided with information as to the location of the point at which the portion of the first amount of detection radiation which is reflected by the surface of the vessel (which in this case corresponds to the third amount of detection radiation).

In some embodiments, the second and third amounts of radiation which are incident on the sensor arrangement may be such that they are not discrete. That is to say, the second and third amounts of radiation may be incident on the sensor arrangement such that they overlap. In such embodiments, instead of determining the measure indicative of the distance between the surface of the liquid and the surface of the vessel by measuring the distance between the location at which the second amount of detection radiation is incident on the sensor arrangement and the location at which the third amount of detection radiation is incident on the sensor arrangement, the controller may determining the measure indicative of the distance between the surface of the liquid and the surface of the vessel by measuring a characteristic of the overlapping second and third amounts of detection radiation. For example, the characteristic may be a width or a shape of the overlapping second and third amounts of detection radiation. In the case where the measured characteristic of the overlapping second and third amounts of detection radiation is a width of the overlapping second and third amounts of detection radiation, it may be the case that the greater the width of the overlapping second and third amounts of detection radiation, the greater the depth of liquid at the depth sensing location.

In some embodiments it has been found that if the position at which the second amount of detection radiation is incident on the sensor arrangement is plotted against the depth of liquid at the depth sensing location, the gradient of the plot differs depending on whether the liquid at the liquid depth sensing location is transparent or opaque. Consequently, in some embodiments, the controller determine whether a liquid at the liquid depth sensing location is transparent or opaque based on the change in position at which the second amount of detection radiation is incident on the sensor arrangement which occurs for a given change in the depth of the liquid at the liquid depth sensing location.

It has been found that some embodiments of the liquid depth sensor are adversely affected by being subjected to a change in temperature. For example, a change in temperature of an optical component in the path of the first amount of detection radiation or second amount of detection radiation may result in a change in direction of the second amount of detection radiation and thereby result in a change in the position at which the second amount of detection radiation is incident upon the sensor arrangement. It will be appreciated that this may lead to an inaccurate measure indicating the depth of the liquid as determined by the processor.

One potential way of minimising or eliminating any error in the depth of the liquid determined by the controller of the liquid depth sensor is to include a temperature regulating device as part of the liquid depth sensor. The temperature regulating device may be configured to maintain the temperature of at least one of the components of the liquid depth sensor substantially constant. Temperature regulating devices are well-known within the art and so further details of the operation of the temperature regulator are omitted.

Another possible way of minimising any error which may occur in the determination of a measure of the depth of the liquid carried out by the liquid depth sensor due to temperature variations or other variations in the operating parameters of the liquid detection sensor (e.g. fluctuations in the characteristics of the first amount of detection radiation produced by the radiation source) is to include a reference channel within the liquid detection sensor.

In one embodiment the liquid depth sensor includes a reference channel. In one embodiment the reference channel includes a second radiation source which produces a fourth amount of detection radiation. The second radiation source is configured, in use, to direct the fourth amount of detection radiation so that it is incident upon a reference surface. The reference surface is preferably a surface which is reflective of the fourth amount of detection radiation. The reference surface is located a fixed (ignoring thermal effects) path length from the second radiation source.

The reference channel further comprises a second sensor arrangement which is arranged to receive a fifth amount of detection radiation. The fifth amount of detection radiation is a portion of the fourth amount of detection radiation which is reflected by the reference surface. In a similar manner to that of the second amount of detection radiation, the position at which the fifth amount of detection radiation is incident on the second sensor arrangement is dependent on a path length between the second radiation source and the reference surface.

The second sensor arrangement is further configured to output a sensor signal indicative of the position at which the fifth amount of detection radiation is incident on the second sensor arrangement. The controller of the liquid depth sensor is configured to receive the sensor signal indicative of the position at which the fifth amount of detection radiation is incident on the second sensor arrangement and determine a measure indicative of a change in path length between the second radiation source and the reference surface based on the sensor signal indicative of the position at which the fifth amount of detection radiation is incident on the second sensor arrangement. In some embodiments the second sensor arrangement may measure at least one other operating characteristic of the second radiation source (e.g. the intensity of the radiation output by the second radiation source) and hence produce a signal indicative of a change in said at least one other operating characteristic of the second radiation source.

Due to the fact that the path length between the second radiation source and the reference surface is substantially constant (excluding laser pointing and thermal effects) then any change in the position at which the fifth amount of detection radiation is incident on the second sensor arrangement will be dependent upon the condition of the liquid depth sensor.

For example, the position at which the fifth amount of detection radiation is incident on the second sensor arrangement may be dependent upon a change in temperature of the liquid depth sensor and hence a thermally induced change in path length between the second radiation source (and/or the second sensor arrangement) and the reference surface. In addition or in the alternative, any change in the position at which the fifth amount of detection radiation is incident on the second sensor arrangement may be caused by variation of other aspects of the liquid depth sensor.

For example, the position at which the fifth amount of detection radiation is incident on the second sensor arrangement may change as a function of characteristics of the second radiation source. For example, if the direction of propagation of the fourth amount of detection radiation produced by the second radiation source changes then this will produce a change in the position in which the fifth amount of detection radiation is incident on the second sensor arrangement.

If, as is the case in some liquid depth sensors, the second radiation source producing the fourth amount of detection radiation and the first radiation source producing the first amount of detection radiation are one and the same, then any fluctuation in characteristics of the radiation source will be measured by both the first sensor arrangement and the second sensor arrangement. Such fluctuations in the radiation source are not just limited to fluctuations in the direction of the protection radiation produced by the radiation source, but extends to other fluctuations such as fluctuations in power of the radiation source or multimoding of the radiation source.

Consequently, the reference channel may be used to determine if a characteristic of the liquid depth sensor has fluctuated in a manner which may result in an error in the measure indicative of the liquid depth determined by the controller. For example, if a change in path length between the second radiation source and reference surface is detected then this may be the result of a thermal change which has affected the reference channel. Such a thermal change may have also affected the path length between the first source producing the first amount of detection radiation and the surface of any liquid (if present) within the vessel. Consequently, the thermal change may have affected the position at which the second amount of detection radiation is incident on the sensor arrangement and hence the measure of liquid depth determined by the controller.

The controller may be configured to correct the measure indicative of the depth of the liquid determined by the controller of the liquid depth sensor based on the output of the reference channel produced by the second sensor arrangement.

In some embodiments, the reference channel may be affected by characteristics of the second radiation source itself, such as the direction of propagation of the fourth amount of detection radiation produced by the second radiation source. If the second radiation source and the radiation source producing the first amount of detection radiation are one and the same then a change in the propagation direction of the first amount of detection radiation which will affect the measurement made by the first sensor arrangement will also cause a change in the propagation direction of the fourth amount of detection radiation which will be measured by the second sensor arrangement. The controller of the liquid depth sensor may then use the signal produced by the second arrangement in order to correct any error in the measurement indicative of the depth of the liquid determined based on the sensor arrangement. That is to say, in some embodiments, the controller may be configured to calculate a corrected measure indicative of the depth of the liquid based on the sensor signal indicative of the position at which the second amount of detection radiation is incident on the sensor arrangement and based on the sensor signal indicative of the position at which the fifth amount of detection radiation is incident on the second sensor arrangement.

In addition, if the first radiation source (which produces the first amount of detection radiation) and the second radiation source (which produces the fourth amount of detection radiation) are one and the same then fluctuations in other operational parameters of the radiation source will be measured by both the first sensor arrangement and second sensor arrangement.

For example, as previously discussed, in some embodiments, the first and second sensor arrangements may be configured so as to measure at least one other property of the second and fifth amounts of detection radiation. The first and second sensor arrangements may be configured to measure the intensity distribution or position of the respective amounts of detection radiation and/or the total intensity of the respective amounts of detection radiation. In this manner, if both the first sensor arrangement and sensor arrangement detects substantially similar fluctuations in intensity distribution of the incident radiation and/or of the total received intensity, then this may be indicative of the radiation source multimode-ing or of a fluctuation in the power of the radiation produced by the radiation source. The controller may then be configured to output a signal which is indicative of suboptimal operation of the radiation source, for example multimoding or a fluctuation in power of the radiation source.

Some embodiments of the liquid depth sensor may be adversely affected by a change in temperature of the vessel to which the liquid depth sensor is mounted and/or by a change in temperature of the fluid within the vessel. Some embodiments may include a temperature signal which outputs a signal which is indicative of a temperature of the vessel and/or a temperature of the fluid within the vessel. The temperature sensor may be used to obviate or mitigate an adverse effect which occurs due to a change in temperature of the vessel and/or of the fluid within the vessel. One way in which this may be achieved is that the liquid depth sensor may be calibrated using the temperature sensor. In order to calibrate the liquid depth sensor a known depth of liquid is placed at the depth sensing location. The temperature of the vessel and/or of the fluid within the vessel is then changed (or allowed to vary). The output of the temperature sensor and the measure indicative of the depth of the liquid at the depth sensing location are monitored by the controller. The controller can then determine how the measure indicative of the depth of the liquid at the depth sensing location changes as a function of the temperature of the vessel and/or of the fluid within the vessel measured by the temperature sensor. The controller may be configured to correct the measure indicative of the depth of the liquid determined by the controller of the liquid depth sensor based on the output of the temperature sensor.

Figure 11:
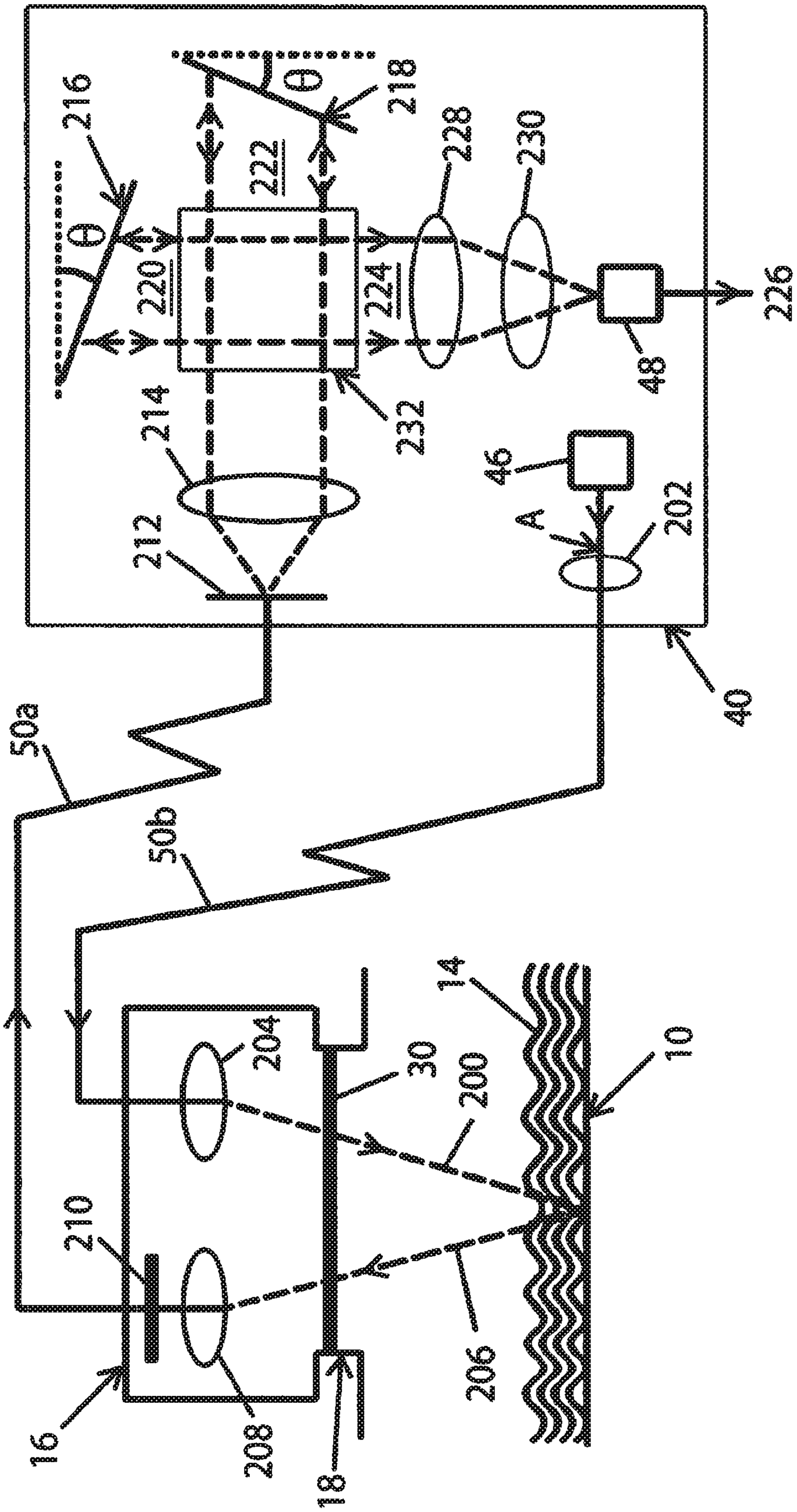
FIG. 11 shows a schematic view of a portion of an optical chemical analyser in accordance with an embodiment of the present invention.

FIG. 11 shows a schematic diagram of an optical chemical analyser which may form part of an embodiment of the present invention. As previously discussed in relation to FIG. 5, the optical chemical analyser comprises a source 46 of a first amount of radiation and a detector 48. The radiation source 46 and detector 48 are located in an off-pipe unit indicated schematically by a dashed box 40.

The optical chemical analyser also includes an on-pipe unit 16. The on-pipe unit 16 is mounted to a vessel which in this case is a gas pipeline 10. The on-pipe unit 16 may be mounted to the gas pipeline 10 in any appropriate manner. For example, it may be mounted via a spur pipe 18 in combination with either of the arrangements shown in FIG. 3 or FIG. 4.

As previously discussed, the off-pipe unit 40 may be located remotely to the on-pipe unit. For example, the off-pipe unit 40 may be located in excess of at least one of about 5 metres, about 10 metres, about 30 meters and about 100 metres from the on-pipe unit 16.

In some embodiments a single off-pipe unit may be connected to a plurality of off-pipe units such that the single off-pipe unit can communicate with/control a plurality of on-pipe units centrally. The cooperation of each on-pipe unit with the central off-pipe unit is as previously described.

The on-pipe unit 16 is linked to the off-pipe unit by at least two optical fibres 50*a* and 50*b*.

In more detail, in the embodiment shown in FIG. 11, the radiation source 46 is configured to direct a first amount of radiation via an optics module so that the first amount of radiation 200 is incident on or passes through a target at a target location. In this case, the target may include a liquid 14 located at the bottom of the vessel (gas pipeline 10) and/or the gas in the vessel (gas pipeline 10). The gas in the gas pipeline in some instances may include a vaporised, or particulate contaminant or a contaminant supported by the gas is an aerosol.

In the embodiment shown in FIG. 11, the optics module may be said to include optics which form part of the off-pipe unit (represented schematically by 202), the optical fibre 50*b* and optics which form part of the on-pipe unit (indicated schematically by 204). The optics module is further configured to receive a second amount of radiation 206 from the target and direct the second amount of radiation to a spatial interference Fourier transform (SIFT) module. In this embodiment, the optics module includes optics which form part of the on-pipe unit 16 which are indicated generally as 208, a first edge filter 210 which is part of the off-pipe unit 16, the optical fibre 50*a*, a second edge filter 212 which is part of the off-pipe unit 40 and optics which form part of the off-pipe unit 40 indicated generally as 214.

It will be appreciated that any appropriate optics 202, 204, 208 and 214 may be used within the optics module provided that the optics module directs the first amount of radiation produced by the radiation source 46 such that it is incident on or passes through a target location, and such that the optics module can receive a second amount of radiation from the target and direct the second amount of radiation to the SIFT module.

The radiation source and optics module (for example, optics which form part of the off-pipe unit and/or optics which form part of the on-pipe unit) may be configured such that the first amount of radiation is an expanded beam of radiation. For example, in one embodiment the radiation source may be a laser and the radiation source and optic module may be configured such that the diameter of the first amount of radiation when it is incident on the target location is about 16 or about 22 mm.

In some embodiments of optical chemical analyser according to the present invention, the diameter of the first amount of radiation when it is incident on the target location is significantly greater than that of the amount of radiation incident on a target which is used to excite Raman scattered radiation in conventional Raman spectroscopy. In conventional Raman spectroscopy the diameter of the amount of radiation incident on a target location which is used to excite Raman scattered radiation is usually much less than 1 mm. This is because, in conventional Raman spectroscopy, it is necessary to maximise the energy density of the amount of radiation which is used to excite Raman scattered radiation. Maximising the energy density of the amount of radiation which is used to excite Raman scattered radiation results in the energy density of the produced Raman scattered radiation being maximised. In conventional Raman spectroscopy, optics are then used to receive the Raman scattered radiation from the very small area target location upon which the amount of radiation which is used to excite Raman scattered radiation is incident.

The ability of an optical chemical analyser according to an embodiment of the present invention to use an expanded beam of radiation which is incident at the target location means that a greater area of target location is illuminated by the expanded beam of radiation than compared to the area of target location that would be illuminated by the Raman exciting radiation used by a conventional Raman spectrometer. Because the illuminated area of target location is greater within the present invention as compared to that of a conventional Raman spectrometer, it is possible for an optical chemical analyser according to the present invention to, at any given moment, analyse a larger area compared to a conventional Raman spectrometer. The ability to analyse a greater area makes it more likely that a localised substance will be located within the analysed area and therefore be detected.

In the embodiments shown in FIG. 11 the SIFT module includes a first dispersive element 216 and a second dispersive element 218. The SIFT module is configured such that a portion 220 of the second amount of radiation is received by the first dispersive element 216. Furthermore, the SIFT module is configured such that a portion 222 of the second amount of radiation is received by the second dispersive element 218. The portions of radiation 220 and 222 which are received by the first dispersive element 216 and second dispersive element 218 respectively are subsequently allowed to interfere with one another so as to form an interference pattern. The radiation indicated by 224 within FIG. 11 includes the interference pattern which has been formed by the interference of said portion of the said amount of radiation received by the first dispersive element and said portion of the second amount of radiation received by the second dispersive element.

The detector 48 is configured to capture an image of at least a portion of the interference pattern present within the radiation 224. The detector is further configured to produce a detector signal 226 based on the captured image of said at least a portion of the interference pattern.

A processor (not shown in FIG. 11, but indicated as 52 within FIG. 5) is configured to receive the detector signal 226 from the detector 48 and perform a transform (e.g. a Fourier transform) on the image of said at least a portion of the interference pattern which forms part of the detector signal 226 to thereby obtain a frequency spectrum of the second amount of radiation 206. The processor may be configured to process the frequency spectrum of the second amount of radiation and thereby identify the presence of a substance in the target and/or determine a concentration of a substance in the target in a manner which is well understood to a person skilled in the art of spectrometry.

Within the embodiment shown in FIG. 11, the detector captures an image of at least a portion of the interference pattern present in radiation 224 via optics 228 and 230.

The SIFT module which forms part of the optical chemical analyser may be used in conjunction with any appropriate type of spectrometry.

In the example shown in FIG. 11, the SIFT module forms part of a Raman spectrometer. That is to say, the optical chemical analyser shown in FIG. 11 includes a Raman spectrometer. When the SIFT module is used as part of a Raman spectrometer the radiation source 46 which produces the first amount of radiation may be a substantially monochromatic and substantially coherent radiation source. For example, the radiation source may be a laser, however, it will be appreciated that any substantially monochromatic and substantially coherent radiation source may be used. In some embodiments, the radiation source may be a 785 nm laser having a power output of 400 mW.

In the case or Raman spectrometry, the second amount of radiation 206 which is received from the target will be Raman scattered radiation. The second amount of radiation, also referred to as the second amount of Raman scattered, may be produced by excitation of the target by the first amount of radiation.

In the case where the vessel is a gas pipeline it would not be obvious to use Raman spectroscopy in order to measure the presence or concentration of a substance within the gas pipeline. This is particularly the case with a liquid located at a stand-off location such as at the bottom of the gas pipeline. The reason for this is that the gas pipelines are typically of a relatively large diameter (e.g. 1.8 m). The signal produced by Raman-scattered radiation is many magnitudes weaker than the signal that would be produced by the use of other types of spectroscopy, e.g. absorption spectroscopy. Consequently, the person skilled in the art would not consider using Raman spectroscopy due to the fact that it is very difficult to measure the Raman-scattered radiation over the substantial distance that the radiation has to travel in order to be measured by a detector which is at a stand-off location exterior to the gas pipeline. This problem may also be exacerbated in some cases by the need for the Raman-scattered radiation to pass through a relatively narrow spur pipe before passing to a detector. The fact that the Raman-scattered radiation has to pass through a narrow pipe/window further minimises the amount of Raman-Scattered radiation which may be received by the detector, thus making it more difficult for the detector to measure the Raman-scattered radiation. The less Raman-scattered radiation received by the detector, the more difficult it will be for a detector to measure the Raman-scattered radiation. That is to say, conventional Raman spectrometers would not capture sufficient photons to facilitate the capture of full spectra when working in stand-off applications.

The inventors have realised that by using a SIFT module which includes dispersive elements as part of the interferometer as opposed to mirrors (which tend to be used in other forms of spectrometry), it is possible to achieve a high etendue system with greater signal throughput which enables Raman spectroscopy to be used even over relatively large distances over which the measurement of Raman-scattered radiation using a conventional interferometer would be infeasible to measure.

Furthermore, in comparison to absorption spectroscopy, it has been found that the measurements made by Raman spectroscopy are invariant to pressure. On the contrary, measurements taken using absorption spectroscopy result in peak positions within the absorption spectrum spreading out (in the frequency domain) with increasing pressure. However, the peaks obtained in the Raman spectrum do not. Consequently, measurements using Raman spectroscopy (unlike absorption spectrometry) can be used in environments in which the pressure of the target or within the vessel may vary, without having to be concerned as to the effect that such a variance in pressure may cause.

In addition if the vessel contains gas at high pressure (e.g. if the vessel is a gas pipeline at high pressure) it would not be obvious to use Raman spectroscopy in order to measure the presence or concentration of a substance within the gas pipeline. That is to say, it would not be obvious to utilise Raman spectroscopy when the target is located in a gas in a high pressure environment. This is because it is common for gases at high pressure to have a refractive index which undergoes significant variation as a function of temperature (as compared to that for the same gas at atmospheric pressure). It follows that, for a gas at high pressure, relatively small local fluctuations in the temperature of the gas may result in significant changes the refractive index of the gas. This may result in unpredictable perturbation of radiation which passes through the gas. This may be referred to as "heat haze". This phenomenon is significant when considering the use of Raman spectroscopy.

As previously discussed, the signal produced by Raman-scattered radiation is many magnitudes weaker than the signal that would be produced by the use of other types of spectroscopy, e.g. absorption spectroscopy. This is because the amount of Raman-scattered radiation which is produced as a function of the amount of radiation used to excite the Raman-scattered radiation is low. This problem is further exacerbated by the fact that, although, in general, the radiation used to excite the Raman-scattered radiation comes from a particular direction, the Raman-scattered radiation is emitted isotropically. This means that if a detector has to collect Raman-scattered radiation which is emitted in a particular direction, then it will only collect a small portion of the total emitted Raman-scattered radiation.

In order to maximise the produced by Raman-scattered radiation signal, it is common in conventional Raman spectroscopy to focus the radiation used to excite the Raman-scattered radiation so that it has a diameter of much less than 1 mm when it is incident on the target. This results in relatively large energy density of the radiation used to excite the Raman-scattered radiation at the target location. The relatively large energy density of the radiation used to excite the Raman-scattered radiation at the target location results in a relatively high energy density of Raman-scattered radiation being produced at the target location. Conventional Raman spectrometers utilise high magnification optics in order to focus on the small (much less than 1 mm diameter) area of the target which is illuminated by the radiation used to excite the Raman-scattered radiation, and hence from which Raman-scattered radiation is emitted. This enables the conventional Raman spectrometer to capture as much of the produced Raman-scattered radiation as possible.

As previously discussed, for a gas at high pressure, relatively small local fluctuations in the temperature of the gas may result in corresponding significant changes in the refractive index of the gas. This is particularly relevant in conventional Raman spectrometers because, as discussed above, conventional Raman spectrometers focus on a very small area of the target. The highly directional return signal (Raman-scattered radiation) may be perturbed by local variations in the refractive index of the gas due to fluctuations in the temperature of the gas. Such perturbations in the return signal may be sufficient to result in the return signal not being received by the spectrometer, thereby resulting in the spectrometer being unable to function correctly. Similarly, the radiation used to excite the Raman-scattered radiation may be perturbed by local variations in the refractive index of the gas due to fluctuations in the temperature of the gas. Such perturbations may result in the radiation used to excite the Raman-scattered radiation not exciting the Raman-scattered radiation at the position at which the spectrometer is focused on in order to receive the return signal. Again, this may result in the spectrometer being unable to function correctly.

It follows that, due to relatively small local fluctuations in temperature of a gas at high pressure resulting in corresponding significant changes to the refractive index of the gas, a person skilled in the art would not consider using Raman spectroscopy in conjunction with a gas at high pressure.

The inventors have discovered that by using a SIFT module it is possible to achieve a high etendue system which uses an expanded radiation beam to excite the Raman-scattered radiation. The use of a SIFT module also does not require focusing on a very small area of target to return a useful signal. As such the inventors have developed a Raman system which, by utilising a SIFT module, is not significantly adversely affected by local changes to the refractive index of a high pressure gas as a result of local variations in temperature of the gas. Consequently, the inventors have developed an inventive system which enables the use of Raman spectrometry in conjunction with a high-pressure gas environment that does not use a probe or intrude into the pipeline.

The SIFT module may be used with any appropriate spectrometer.

When the SIFT module is utilised as part of a certain types of spectrometer (for example a Raman spectrometer), the optics module may further comprise a suppression filter configured to substantially prevent a component of the second amount of radiation which has a frequency which is substantially the same as the frequency of the first amount of radiation from reaching the SIFT module. This is because the first amount of radiation (i.e. the radiation produced by the radiation source 46) does not contain any useful information about properties of the target. In fact, in the absence of a suppression filter, it may be the case that if a component of the second amount of radiation which has a frequency which is substantially the same as a frequency of the first amount of radiation reaches the SIFT module then this component of the second amount of radiation may overwhelm the detector such that information relating to the target (for example present in Raman scattered radiation) is not measurable by the detector. This may mean that the detector is incapable for functioning so as to identify the presence of a substance in the target and/or to determine a concentration of a substance in the target.

In present embodiment the suppression filter includes two edge filters 210 and 212. The edge filter 210 is located at a first end of the optical fibre 50*a* (and in this case is located within the on-pipe unit 16). The second edge filter 212 is located at a second end of the optical fibre 50*a* (and in this case is located within the off-pipe unit 40).

It is common for systems which incorporate an edge filter and an optical fibre to have one or more edge filters located only at one end of the optical fibre. One reason for this is that it may be disadvantageous in terms of space configuration to locate an edge filter at either side of the optical fibre.

The inventors have discovered that, surprisingly, optical fibres produce a small amount of fluorescence. Radiation produced by fluorescence within the optical fibre may be sufficient to be detected by the detector and hence cause an error in the frequency spectrum of the second amount of radiation which is calculated by the processor. This is because the processor may receive radiation which has been produced by fluorescence of the optical fibre and assume that it has been produced by the target.

It has been found that, surprisingly, if an edge filter is located at each end of the optical fibre then the amount of radiation which is produced by fluorescence within the optical fibre is reduced to a much greater level than that of when one or more edge filters is used only at a single end of the optical fibre. Minimising the amount of radiation which reaches the SIFT module that has the same wavelength as the first amount of radiation, and minimising the amount of radiation which reaches the SIFT module which has been produced by fluorescence in the optical fibre may lead to less unwanted radiation reaching the detector. Consequently, this will result in a more accurate frequency spectrum of the second amount of radiation being calculated by the processor.

There are generally two types of edge filter: long wave pass edge filters and short wave pass edge filters. The construction of an edge filter is well known to a person skilled in the art and, as such, further discussion of the construction of the edge filters is omitted.

Both long wave pass edge filters and short wave pass edge filters have what is referred to as a cut-off wavelength. Long wave pass edge filters are configured such that they are relatively transparent to radiation of a wavelength which is greater than the cut-off wavelength, and are relatively opaque or reflective to radiation having a wavelength which is shorter than the cut-off wavelength. Conversely, a short wave pass edge filter is configured such that it is relatively transparent to radiation having a wavelength that is shorter than the cut-off wavelength, and is relatively opaque or reflective to radiation having a wavelength which is greater than the cut-off wavelength.

In some embodiments, the edge filters 210 and 212 may be arranged such that the edge filters are both long wave pass edge filters or both short wave pass edge filters. If both of the edge filters are long wave pass edge filters than the cut-off wavelength of the edge filters may be chosen such that it is a longer wavelength than the wavelength of the first amount of radiation. Likewise, if both of the edge filters are short wave pass edge filters than the cut-off wavelength of the edge filters may be chosen such that it is a shorter wavelength than the wavelength of the first amount of radiation.

In other embodiments, other edge filter arrangements may be used. For example, edge filters 210 and 212 may be arranged such that the edge filter at one end of the optical fibre (for example the edge filter 210) is one of a long wave pass edge filter or short wave pass edge filter, and the edge filter at the second end of the optical fibre (for example edge filter 212) is the other of a long wave pass edge filter or a short wave pass edge filter. The cut-off wavelengths of the edge filters may be chosen such that the cut-off wavelength of the long wave pass edge filter is less than the cut-off wavelength of the short wave pass edge filter. In this way, the combination of the long wave pass edge filter and short wave pass edge filter will be so as to be relatively transparent to radiation which has a wavelength within the band defined between the cut-off wavelength of the long wave pass edge filter and the cut-off wavelength of the short wave pass edge filter. The cut-off wavelengths of the long and short wave pass edge filters may be chosen such that radiation which has a frequency/wavelength which is substantially the same as that of the first amount of radiation is substantially attenuated by the edge filters, whereas radiation which has a frequency which is useful if determining the spectra of the target is substantially unattenuated by the edge filters.

Although the embodiment described above utilises edge filters at the first and second ends of the optical fibre, in other embodiments, any appropriate filters may be used to minimise the amount of radiation which reaches the SIFT module that has the same wavelength as the first amount of radiation, and/or to minimise the amount of radiation which reaches the SIFT module which has been produced by fluorescence in the optical fibre. For example, band stop or notch filters may be used. Band stop or notch filters are configured such that they attenuate a predetermined band of radiation. For example a band stop or notch filter may be configured to substantially attenuate radiation within a band having upper and lower frequency limits. The filter is also configured to allow radiation with a frequency above the upper frequency and below the lower frequency to pass through it relatively un-attenuated.

In some arrangements which include a first optical filter located at a first end of the optical fibre and a second optical filter located at the second end of the optical fibre (as discussed above) at least one of (and in some cases both of) the first and second optical filters are orientated such that a normal to a surface of the optical filter upon which radiation is incident is non parallel to the direction of propagation of said incident radiation. In other words, a normal to a surface of the optical filter upon which radiation is incident is non parallel to (or subtends an angle with respect to) an optical axis along which the radiation travels. This may also be referred to as the optical axis of the optical filter being non-parallel (or subtending an angle with respect to) an optical axis along which the radiation travels.

In this way, any of the radiation which is incident on the optical filter which is reflected by the filter will be reflected in a direction which is different to the direction of the radiation incident on the optical filter. Consequently, radiation which is reflected by the optical filter will not travel along the same path (in the opposite direction) as the incident radiation. This may be advantageous in applications in which the reflected radiation, if incident on the target, may cause the target to emit unwanted radiation which may result in unwanted radiation reaching the detector, thereby resulting in inaccuracies in the frequency spectrum of the second amount of radiation being calculated by the processor. Consequently, in such applications, if the optical axis of the optical filter is non-parallel with the optical axis of radiation incident upon it, then any radiation which has travelled from the target location, which is incident on the optical filter and which is reflected by the optical filter, will be reflected by the optical filter in a direction such that the reflected radiation is not incident on the target location.

An arrangement whereby a first optical filter located at a first end of the optical fibre and a second optical filter located at the second end of the optical fibre as discussed above may form part of any appropriate spectrometer, where discussed in this document or otherwise.

Within the embodiment shown in FIG. 11, the SIFT module includes a beam splitting apparatus 232. Any appropriate form of beam splitting apparatus may be used. In this embodiment the beam splitting apparatus comprises a beam splitter cube. The beam splitting apparatus is configured to split the second amount of radiation into the portion of the second amount of radiation which is received by the first dispersive element 216 and the portion of the second amount of radiation which is received by the second dispersive element 218.

The first and second dispersive elements 216, 218 are configured such that they cause spatial separation of the radiation incident upon them based upon the frequency of the radiation. That is to say, the dispersive elements are configured such that if the radiation incident upon them has a spectrum of frequencies, then the dispersive elements will separate the radiation in a spectrum of directions, each direction within the spectrum of directions corresponding to a frequency in the spectrum of frequencies.

Any appropriate dispersive element may be used for the first and second dispersive elements (provided that they cause spatial separation of the radiation incident upon them based upon the frequency of the radiation). Examples of suitable dispersive elements include a prism or a grating.

The embodiment shown in FIG. 11 has first and second dispersive elements which are first and second diffraction gratings respectively.

The first and second diffraction gratings 216, 218 are oriented so that the plane of each of the first and second diffraction gratings 216, 218 is non-perpendicular with respect to an optical axis of the portions 220, 222 of the second amount of radiation that are received by the first and second diffraction gratings 216, 218 respectively. In particular, the angle subtended between the normal to the plane of each of the first and second diffractions gratings the optical axes of the respective portions of the second amount of radiation is the Littrow angle θ. In this case, θ is given by rearranging the equation:

$$m\lambda=2d\sin\theta \quad (5)$$

where λ is the wavelength of the radiation, m is the order of diffraction (which has an integer value) and 1/d is the grating line density.

Radiation interacts with the diffraction gratings according to the equation:

$$k(\sin(\theta)+\sin(\theta-\omega))=\frac{m}{d} \quad (6)$$

where ω is the diffraction angle with respect to Littrow for radiation with a wavenumber k.

It will be appreciated that other types of dispersion element, such as prisms, may not need to be angled with respect to the optical axes of the respective portions of the second amount of radiation.

For a given configuration of dispersive element (e.g. diffraction grating), the spectral range SR (in wavenumbers) of the configuration is given by:

$$SR=\frac{0.01P_D}{2\theta R} \quad (7)$$

where $P_D$ is the number of pixels of the detector which measure the diffraction and R is the resolving power of the configuration.

If the Littrow wavelength of the diffraction gratings is set to 920 nm, then with a 12 mm aperture diffraction grating, 200 lines per millimetre are required on the gratings to cover a desired spectral range of 801 nm to 1052 nm. This spectral range is sufficient to cover the expected Raman radiation produced by liquid contaminants (e.g. glycols, methanol, amines, gas condensates and/or compressor oils) which may be present in a gas pipeline. It will be appreciated that, in other embodiments, any appropriate aperture of diffraction grating and/or number of lines per millimetre of the diffraction gratings may be used in order to cover the desired spectral range for a given Littrow wavelength.

In one embodiment the detector 48 is a back-illuminated CCD having dimensions of 26.4 mm by 2 mm upon which the interference pattern present within the radiation 224 is imaged. Although the detector described in this embodiment is a CCD detector, it will be appreciated that in other embodiments any appropriate sensor may be used. For example, a CMOS sensor may be used.

In this embodiment two cylindrical lenses 228 and 230 are used to form an image of the interference pattern present within the radiation 224 on the detector having the correct size.

Figure 12:
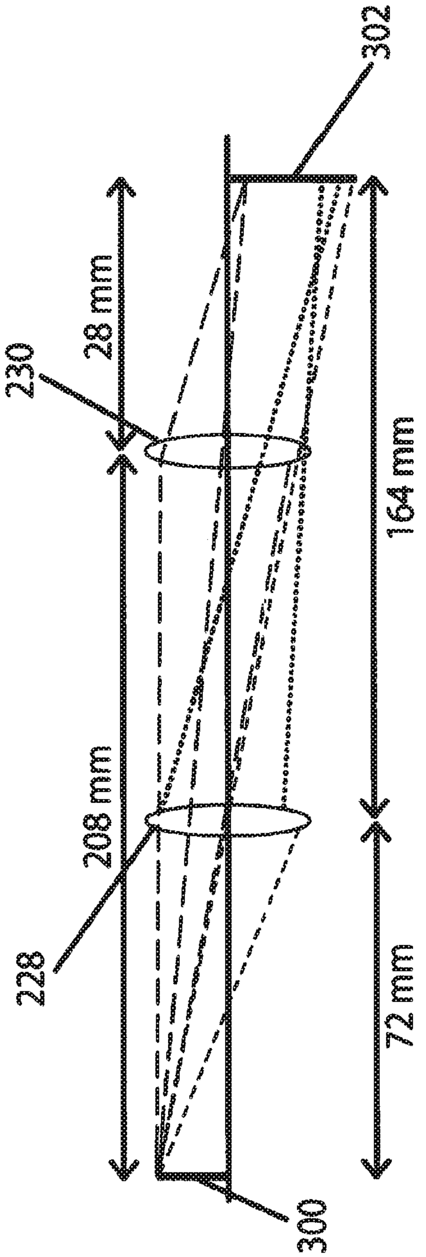
FIG. 12 shows a schematic view of a lens arrangement which may form part of an optical chemical analyser as shown in FIG. 11.

FIG. 12 shows a schematic representation of the cylindrical lenses 228 and 230. In this embodiment the object 300 is the surface of each of the first and second dispersive elements (in this case the first and second diffraction gratings). The object 300 is located 72 mm from the first cylindrical lens 228. If the size of the object 300 is approximately 12 mm (e.g. due to the 12 mm aperture of the diffraction gratings), then to be imaged correctly on the detector (which has dimensions 26.4 mm×2 mm) the image must be approximately twice as large in one axis (corresponding to the 26.4 mm dimension of the detector) and approximately 0.16 of the size in the other axis (i.e. corresponding to the 2 mm dimension of the detector).

The cylindrical lenses 228 and 230 have focal lengths of 50 mm and 25 mm respectively. In this embodiment the cylindrical lens 230 is located 208 mm from the object 300 and the image 302 is formed 28 mm away from the lens 230 on the opposite side of the lens 230 to the object 300. The lens 228 is located 72 mm from the object and forms an image which is 164 mm from the lens 228 and on the other side of the lens 228 compared to the object 300. The combination of lenses shown in FIG. 12 will result in an image formed at the detector which has a size of 25 mm×1.68 mm.

Within the embodiment shown in FIG. 11 the optics 202 and 212 within the off-pipe unit 40 and the optics 208 and 204 within the on-pipe unit 16 may be configured such that the size of any focused spot produced at either of the fibres 50*a*, 50*b* is kept below the aperture of the fibres 50*a*, 50*b*. For example, if the aperture of the fibres is 0.9 mm then the optics may be configured to ensure that any focused spot produced at the fibre is about 0.8 mm in diameter or less. This helps to ensure that the amount of radiation which is lost by not being passed down the optical fibres 50*a*, 50*b* is minimized, thereby increasing the efficiency of the optical chemical analyser.

As previously discussed, embodiments of the optical chemical analyser need not be limited to the inclusion of a Raman spectrometer as described above. The optical chemical analyser may include any appropriate spectrometer. For example, some embodiments of the optical chemical analyser may include an absorption spectrometer.

In some embodiments in which the optical chemical analyser comprises an absorption spectrometer, the source of a first amount of radiation may be configured to produce radiation which is substantially polychromatic. That is to say, the source of the first amount of radiation may be configured to produce radiation which has a spectrum of frequencies.

An embodiment of the optical chemical analyser which includes an absorption spectrometer will also differ from the embodiment in FIG. 11 (which includes a Raman spectrometer) in the following ways. The optical chemical analyser shown in FIG. 11 which incorporates a Raman spectrometer has a SIFT module which enables the processor to obtain a frequency spectrum of the second amount of radiation (i.e. the radiation received from the target). The frequency spectrum determined by the processor enables the spectrum of Raman scattered radiation produced by the target to be measured.

In an optical chemical analyser which incorporates an absorption spectrometer, the SIFT module and processor may be configured to obtain a frequency spectrum of the first amount of radiation (i.e. the radiation supplied to the target) and then compare the frequency spectrum of the first amount of radiation (supplied to the target) and the frequency spectrum of the second amount of radiation (received from the target) in order to produce an absorption spectrum of the target.

In general terms, the SIFT module for an optical chemical analyser including an absorption spectrometer, compared to that of an optical chemical analyser including a Raman spectrometer, will include a further pair of dispersive elements which can receive a portion of the first amount of radiation and thereby produce a second interference pattern which can be imaged by a detector and processed to obtain a frequency spectrum of the first amount of radiation.

In more detail, an optical chemical analyser including an absorption spectrometer may include the features described in relation to an optical chemical analyser having a Raman spectrometer illustrated in FIG. 11 and additionally include the following features. The SIFT module may further comprise a third dispersive element and a fourth dispersive element. The SIFT module may be configured such that a portion of the first amount of radiation is received by the third dispersive element and interferes with a portion of the first amount of radiation received by the fourth dispersive element to form a second interference pattern. Referring briefly to FIG. 11, the portions of the first amount of radiation which are directed so as to be received by the third dispersive element and the fourth dispersive element respectively may be directed from position A along the beam path of the first amount of radiation produced by the source 46 of the first amount of radiation. That is to say, in one embodiment all the components of the SIFT module are located in the off-pipe unit. The SIFT module of an optical chemical analyser including an absorption spectrometer may further comprise a second detector configured to capture an image of at least a portion of the second interference pattern and produce a second detector signal based on the image captured by the second detector.

The processor of the optical chemical analyser is configured to receive the second detector signal from the second detector and perform a Fourier Transform on the second detector signal to thereby obtain a frequency spectrum of the first amount of radiation. The processor may further be configured to compare the frequency spectrum of the second amount of radiation to the frequency spectrum of the first amount of radiation in order to produce an absorption spectrum. For example, the processor may be configured to subtract the frequency spectrum of the first amount of radiation from the frequency spectrum of the second amount of radiation in order to produce an absorption spectrum. The absorption spectrum is the absorption spectrum of the target at the target location.

The processor may be configured to process the frequency spectrum of the absorption spectrum and thereby identify the presence of a substance in the target and/or determine the concentration of a substance in the target.

The processor of an embodiment of an optical chemical analyser (for example any of those discussed above) may also be configured to detect a change in the presence of a desired substance at the target location based on the frequency spectrum of the second amount of radiation (or in the case of an optical chemical analyser including an absorption spectrometer, based on the absorption spectrum) and output a substance present signal when the presence of substance.

For example, in the case where an embodiment of an optical chemical analyser is mounted to a gas pipeline, the processor may be configured to detect the presence of a contaminant (glycols, methanol, amines, gas condensates or compressor oil), or the presence of a contaminant above a predetermined concentration, based on the frequency spectrum. If a contaminant is present or present above a predetermined concentration, then the target detection module may output a substance present signal. The substance present signal may take any appropriate form, but in one embodiment may be an alarm signal provided to the remote terminal 66 shown in FIG. 5. The alarm signal may inform a user that a contaminant is present within the gas pipeline such that use of the gas pipeline can be suspended or such that any components attached to the pipeline or supplied by the pipeline which may be damaged by the contaminants may be protected.

Any of the embodiments of optical chemical analyser discussed above may operate to determine gas or liquid or solid phase species at process pressure in a pipeline or vessel.

Any of the embodiments of optical chemical analyser discussed above may further include a target detection module. The target detection module may be configured to detect a change in the presence of a desired class of target at the target location and output a target present signal when the presence of a desired class of target is detected. The target detection module may include any appropriate sensor to detect any appropriate desired change in presence of a desired class of target at the target location. The target detection module may be configured to detect the presence of a liquid (or an increase in the amount of liquid present). One embodiment including such a target detection module may include a liquid depth sensor as previously discussed. The controller of the liquid depth sensor may determine a measure indicative of the depth of the liquid, and if the presence of liquid is detected by the liquid depth sensor (or if the depth of the liquid increases above a predetermined threshold) then the controller of the liquid depth sensor may output the target present signal.

In some embodiments of optical chemical analyser which incorporate a target detection module, the optical chemical analyser may be configured such that at least a portion of the optical chemical analyser enters a powered-up state from a powered-down state based on the target present signal being output by the target detection module. This is because, in some embodiments, it will not be necessary to identify the presence of a substance (or the concentration of a substance) at the target location unless an appropriate target is located at the target location. Examples of said at least a portion of the optical chemical analyser which enters a powered-up state or a powered-down state may include the source of the first amount of radiation and/or the detector.

Consequently, the at least a portion of the optical chemical analyser may be kept in a powered-down state until a target present signal is output by the target detection module. Hence the at least a portion of the optical chemical analyser may be kept in a powered-down state whilst the desired class of target is either not present at the target location or is present to an extent less than the predetermined amount. This may be advantageous in some applications.

For example, minimising the amount of the optical chemical analyser which is in a powered-up state whilst no sufficient target is present will reduce the energy consumption of the optical chemical analyser because the at least a portion of the optical chemical analyser will not be energised unnecessarily whilst a sufficient target is not present at the target location. In addition, some components of the optical chemical analyser may have a limited operating lifetime. For example, a radiation source, such as a laser, which forms part of the optical chemical analyser may only operate for a fixed number of hours. In this case, by only placing such a component in a powered-up state when a sufficient target is present at the target location, the operational lifetime of this component can be maximised.

In other embodiments, the target detection module may take any appropriate form. For example, the target detection module may include a time-of-flight based distance measuring system. The time-of-flight based distance measuring system may measure the distance to the surface of a liquid within the vessel and may output a target present signal when the distance measured by the distance measuring system is indicative of a depth of liquid within the vessel which fall within a predetermined range, for example, exceeds a predetermined amount. A time-of-flight based distance measuring system operates by measuring the time a portion of radiation takes to travel a certain distance and then, based on a known speed of propagation of the portion of radiation, calculating the distance travelled by the portion of radiation. For example, a time-of-flight based system may be configured to measure the time it take a portion of radiation emitted by an emitter to reflect off the surface of the liquid within the vessel and be received by a receiver.

The target present signal in some cases may be the absence of a signal. For example, in some embodiments, the target detection module may output a signal when no target is detected and the target detection module may cease outputting a signal when a target is detected. In such an embodiment, the cessation of a signal being output by the detection module may be considered to be a target present signal.

Figure 13:
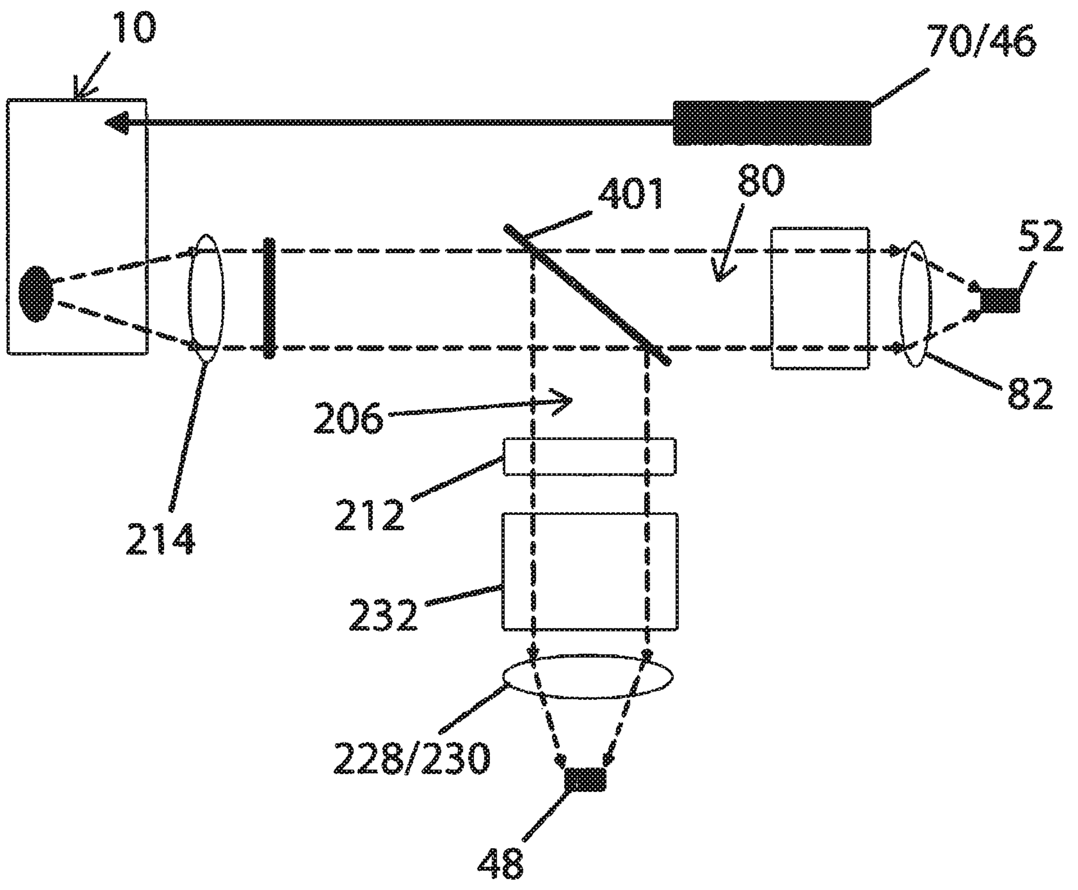
FIG. 13 shows a schematic view of a portion of an optical chemical analyser in accordance with another embodiment of the present invention.

Referring to FIG. 13, in some embodiments which include both an optical chemical analyser as previously discussed and a liquid detection sensor as previously discussed, the optical chemical analyser may include a radiation-directing element 401 which is configured to direct the second amount of radiation 206 to the SIFT module of the optical chemical analyser, and also to direct the second amount of detection radiation 80 to the sensor arrangement of the liquid detection sensor. If the second amount of radiation 206 and the second amount of detection radiation 80 have different wavelengths, then the radiation-directing element may comprise a dichroic filter which allows radiation of the wavelength of one of the second amount of radiation and second amount of detection radiation to pass through it, and which reflects radiation of the wavelength of the other of the second amount of radiation and second amount of detection radiation.

Embodiments of either an optical chemical analyser as previously discussed or a liquid depth sensor as previously discussed may include an imaging device. The imaging device may take any appropriate form and may in some embodiments be a camera. The imaging device may be configured to produce an image of at least a portion of the target (in the case of an optical chemical analyser) or of at least a portion of the depth sensing location (in the case of a liquid depth sensor). In other embodiments the imaging device may be configured to produce an image of another portion of a vessel to which the optical chemical analyser or liquid depth sensor is attached.

The optical chemical analyser or liquid depth sensor may further include an imaging controller which is configured to selectively energise the imaging device based on the detector signal produced by the detector (in the case of an optical chemical analyser) or based on the sensor signal produced by the sensor (in the case of a liquid depth sensor).

For example, when the imaging controller forms part of an optical chemical analyser, the imaging controller may be configured such that it energises the imaging device when the detector of the optical chemical analyser produces a detector signal which is indicative of the presence of a particular substance (for example a contaminant) within the vessel to which the optical chemical analyser is mounted. In another example in which a liquid depth sensor includes an imaging device, the imaging controller may be configured such that it selectively energises the imaging device when the sensor signal produced by the sensor of the liquid depth sensor is indicative of the presence of a liquid within the vessel, or the presence of an amount (depth) of liquid within the vessel which exceeds a predetermined amount.

In some embodiments of an optical chemical analyser, the optics module may be configured to direct the first amount of radiation through a volatile substance (for example gas within a gas pipeline). The first amount of radiation may transfer energy to the volatile substance. The source of the first amount of radiation and the optics module may be configured such that the total energy and/or density of energy transferred to the volatile substance from the first amount of radiation is less than an ignition amount. The ignition amount of total energy and/or density of energy is the total energy and/or density of energy which would be required to be transferred to the volatile substance by the first amount of radiation in order for the first amount of radiation to cause the volatile substance to ignite. It will be appreciated that it is desirable for the optical chemical analyser to be configured such that the first amount of radiation does not cause the volatile substance to ignite whilst it is operating.

Similarly, some embodiments of liquid depth sensor may such that the radiation source is configured to direct the first amount of detection radiation through a volatile substance. The first amount of detection radiation may transfer energy to the volatile substance. The radiation source may be configured such that the total energy and/or density of energy transferred to the volatile substance from the first amount of detection radiation is less than an ignition amount. In a similar manner to before, the ignition amount of total energy and/or density of energy is the total energy and/or density of energy which would be required to be transferred to the volatile substance by the first amount of detection radiation in order for the first amount of detection radiation to cause the volatile substance to ignite. It will be appreciated that it is desirable for the liquid depth sensor to be configured such that the first amount of detection radiation does not cause the volatile substance to ignite whilst it is operating.

Some embodiments of optical chemical analyser or liquid depth sensor may be mounted to a pressurised vessel such as a gas pipeline. In these embodiments the optical chemical analyser or liquid depth sensor may include a window (as shown in FIGS. 3 and 4) through which radiation from exterior to the vessel can pass into the vessel and through which radiation from within the vessel can pass to the exterior of the vessel. In some applications, due to the presence of gas within the vessel, condensation may form on the window. This may be disadvantageous as the condensation may adversely affect the passage of radiation through the window.

For example, the condensation may reflect, absorb and/or redirect radiation passing through the window. For example, in the case of Raman scattered radiation, the condensation may attenuate the Raman scattered radiation signal produced by the target and thereby cause the optical chemical analyser to be unable to correctly determine the frequency spectrum of the Raman scattered radiation produced by the target. In another example, the condensation may cause the path of the second amount of detection radiation to be altered, thereby potentially causing an error in the measure indicative of the depth of the liquid determined by the controller of a liquid depth sensor.

One way to reduce the amount of condensation which forms on the window is to include a heater which is in thermal communication with the window and which is configured to heat the window. In some embodiments the heater may comprise a heating coil which is wrapped around a portion of the optical chemical analyser of liquid depth sensor which is in thermal communication with the window. In other embodiments, any appropriate heater may be used to heat the window. The heater may heat the window such that the temperature of the window is greater than the dew point temperature of the gas within the gas pipeline adjacent the window. Raising the temperature of the window above the dew point of the gas reduces the amount of condensation which forms on the window and thereby mitigates the problems discussed above.

However, surprisingly, the inventors have found that by placing a heater in thermal communication with the window and heating the window, this does not sufficiently solve the problem (i.e. does not sufficiently remove the condensation from the window). The reasoning for this is as follows.

It has been determined that if a heater is used to heat the window, then the heater may also heat the vessel to which the optical chemical analyser or liquid depth sensor is mounted. By heating the vessel, the heater also increases the temperature of the gas within the vessel. Consequently, this causes the dew point temperature of the gas to raise. The raised dew point of the gas means that the heating applied to the window is no longer sufficient to prevent condensation from forming on the window.

A solution to this problem has been found by the inventors as follows. The optical chemical analyser or liquid depth sensor further includes a thermal isolator which thermally isolates the heater from the vessel. By thermally isolating the heater from the vessel, the amount of heat which is inadvertently transferred from the heater to the vessel whilst heating the window is reduced. By reducing the amount of heat which is transferred from the heater to the vessel, the gas within the vessel is heated less. Consequently, the dew point temperature of the gas increases less, thereby enabling the heater to reduce the amount of condensation formed on the window.

In an embodiment in which the optical chemical analyser or liquid depth sensor includes an on-pipe unit which includes the window and the heater, and in which the on-pipe unit is mounted to a vessel in the form of a pipeline including a spur pipe, the thermal isolator may be a seal (for example a phenolic seal or a VCS type seal supplied by GPT, Denver, USA) mounted between the on-pipe unit and spur pipe. For example, in the set-up shown in FIG. 3 the phenolic seal may be sandwiched between the flange portion 32 of the spur pipe and the flange piece 26. In other embodiments, any appropriate thermal insulator may be used. It will be appreciated that, in other embodiments, the thermal isolator may be formed from any appropriate material.

Figure 13A:
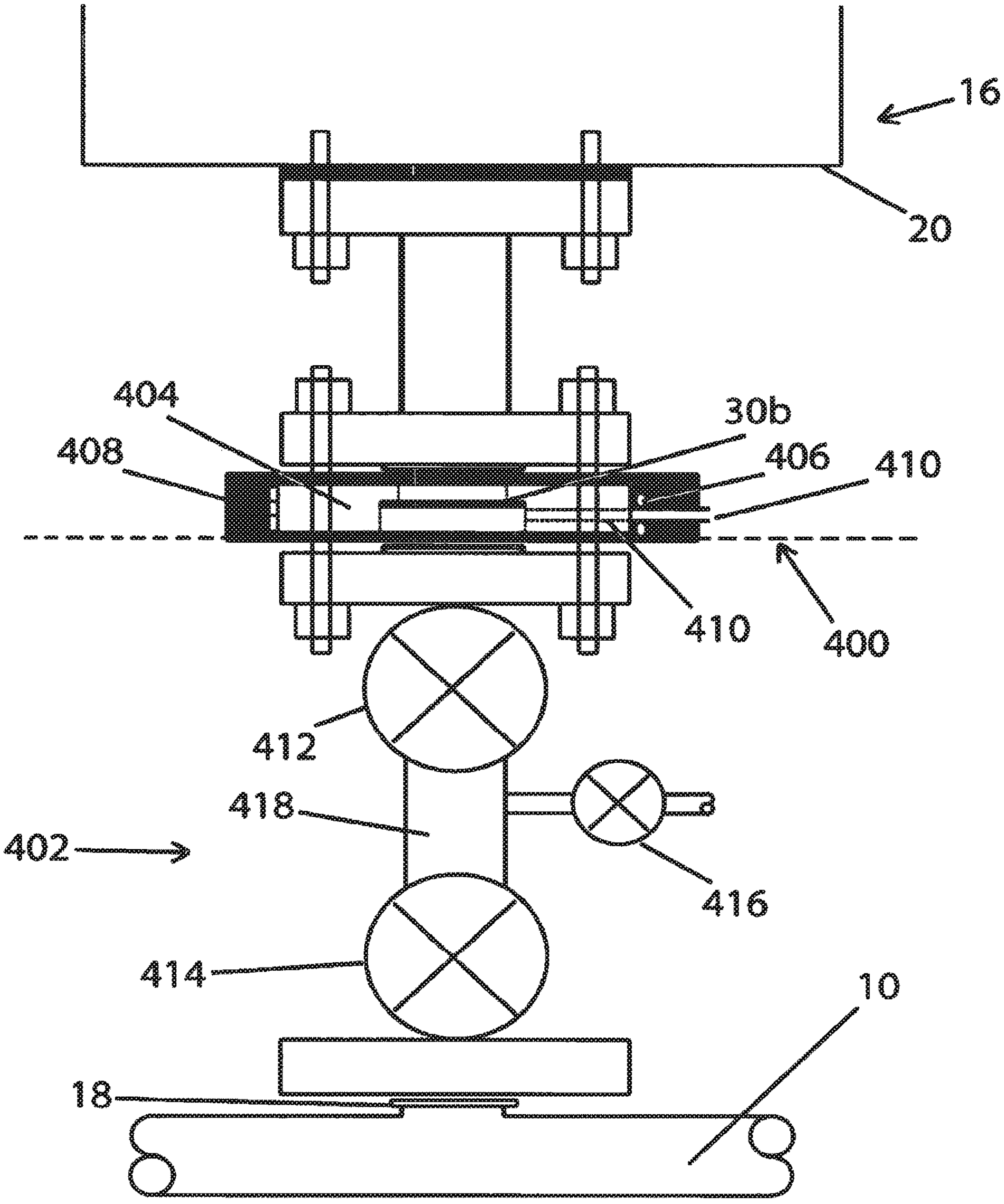
FIG. 13*a* shows a schematic view of a portion of an optical chemical analyser and/or liquid depth sensor in accordance with a further embodiment of the present invention.

Another embodiment which enables the amount of condensation which forms on the window to be reduced is described with regard to FIG. 13*a*.

FIG. 13*a* shows a schematic view of a portion of an optical chemical analyser and/or liquid depth sensor according to an embodiment of the present invention. The casing 20 of the on-pipe unit of the optical chemical analyser and/or liquid depth sensor is mounted to the gas pipeline 10 via a spur pipe 18. A heater assembly 400 and double block and bleed valve assembly 402 are located between the casing 20 and the spur pipe 18. A window 30*b* acts as a fluid seal which separates the on-pipe unit 16 from the gas within the gas pipeline 10 (and hence spur pipe and double block and bleed valve assembly). As previously discussed, the window 30*b* may be formed from any appropriate material. In one example, the window 30*b* is formed of c-cut sapphire which is braised into place within a metal-receiving flange 404.

The heater arrangement 400 includes a heater in the form of heater tape 406 which can be supplied with electrical power so as to increase the temperature of the heater tape 406. The heater tape 406 is wrapped around the receiving flange 404 and is in thermal contact therewith. Consequently, if power is supplied to the heater tape 406 such that the heater tape increases temperature, then heat from the heater tape 406 is conducted into the receiving flange 404. Sapphire has relatively good thermal conducting properties and, as such, heat which is conducted from the heater tape 406 into the receiving flange 404 is thereafter conducted into the window 30*b*, thereby increasing the temperature of the window 30*b*.

The heating assembly 400 also includes an insulation member 408. The insulation member 408 is formed of a thermal insulator and surrounds the heater tape 406 and receiving flange 404 thereby minimising the amount of heat which is conducted away from the heater tape 406 towards the casing 20 or gas pipeline 10. The provision of a heater and insulating member may reduce the amount of condensation which forms on the window as previously discussed. The operation of the heater assembly is as previously discussed.

The heater assembly also includes a vent passage 410. The vent passage 410 enables fluid flow communication between the side of the window closest to the gas pipeline 10 (i.e. the side of the window which is exposed to the fluid within the gas pipeline) and atmosphere. The vent passage 410 passes through the receiving flange 404. The functioning of the vent passage 410 is discussed in more detail below.

The double block and bleed valve assembly 402 which is located between the spur pipe 18 and the on-pipe unit 16 includes first and second main valves 412 and 414 and a bleed valve 416. The double block and bleed valve assembly 402 also includes an intermediate chamber 418 which is intermediate the first and second main valves 412, 414 and the bleed valve 416. The first main valve 412 controls the flow of fluid between the intermediate chamber 418 and the window 30*b* of the optical chemical analyzer and/or liquid depth sensor. The second main valve 414 controls the flow of fluid between the intermediate chamber 418 and pipeline 10 via spur pipe 18. The bleed valve 416 controls fluid flow between the intermediate chamber 418 and a bleed location such as atmosphere. Although the bleed location in this embodiment is the atmosphere, in other embodiments the bleed location may be any appropriate location having gas at any appropriate pressure.

It is thought that, in some applications, the presence of relatively wet atmospheric gas at high pressure (for example at substantially the same pressure as the gas within the pipeline 10) may result in condensation forming on the surface of the window 30*b* which is exposed to the gas. As previously discussed, the formation of condensation on the window may be disadvantageous because the condensation may adversely affect the passage of radiation through the window.

It has been found that the provision of a vent passage 410 may obviate or mitigate this problem. This may be achieved as follows.

In a normal operating condition of the optical chemical analyser and/or liquid depth sensor, the vent passage 410 is in a normal configuration in which it is closed by a closing member (not shown), for example a valve, which prevents the flow of fluid through the vent passage 410, for example between atmosphere and the window 30*b*.

If condensation occurs (or it is thought that there may be atmospheric gas adjacent the window 30*b* which may lead to condensation forming on the window), the vent passage 410 may be placed in an open configuration in which the closing member no longer prevents fluid flow through the vent passage 410 (e.g. between atmosphere and adjacent the window 30*b*). In the case where the pressure of the fluid adjacent the window 30*b* is greater than the pressure of the fluid at the other end of the vent passage 410 (for example the atmospheric pressure of atmosphere), then the fluid adjacent the window 30*b* will pass through the vent passage 410 from adjacent the window 30*b* to the other end of the vent passage 410 (e.g. atmosphere).

In this manner, the relatively wet atmospheric gas adjacent the window 30*b* will be expelled from the system via the vent passage 410 such that the atmospheric gas is no longer adjacent the window 30*b* and is replaced with gas from the gas pipeline. Due to the fact that the relatively wet atmospheric gas is no longer adjacent the window 30*b*, this will reduce or eliminate any condensation which may form on the window 30*b* due to the presence of atmospheric gas. Once the atmospheric gas has been substantially removed from the system, the vent passage 410 can be returned to its normal, closed configuration.

In another embodiment, relatively wet atmospheric gas which is present adjacent the window 30*b* may be removed from the system in a different manner. Referring to the double block and bleed valve assembly 402, in normal operation, both the first and second main valves 412 and 414 will be in an open configuration such that there is a gas flow path between the pipeline 10 (via spur pipe 18) and the window 30*b*. This will also allow radiation which passes through the window 30*b* to pass into the vessel (in this case pipeline 10). Furthermore, the normal operating condition of the double block and bleed valve assembly 402, the bleed valve 416 will be closed such that there is no flow communication between the intermediate chamber 418 (and hence the window 30*b*) and the bleed location.

If condensation is detected on the window 30*b* (or if it is thought that relatively wet atmospheric gas may be present adjacent the window 30*b* potentially leading to condensation forming on the window 30*b*), then the double block and bleed valve assembly 402 may be used to purge the atmospheric gas adjacent the window 30*b* from the system as follows.

The second main valve 414 may be placed in a closed configuration such that there is substantially no fluid flow path between the intermediate chamber 418 and the vessel (in this case pipeline 10). The bleed valve 416 may then be placed in an open configuration such that there is a gas flow path between the bleed location and the intermediate chamber 418. The vent passage 410 is also be placed in an open configuration (i.e. a configuration in which the closing member (not shown) does not prevent fluid flow between adjacent the window 30*b* and the other end of the vent passage 410) such that there is a fluid flow path between adjacent the window 30*b* and the other end of the flow passage 410.

A source of relatively dry gas which will not result in the formation of condensation on the window 30*b* is connected to one of the bleed location or the end of the flow passage 410 other to that which is located adjacent the window 30*b*. Said source of gas is configured such that it is at a higher pressure than the pressure at the other of the bleed location and the end of the flow passage 410 other than that which is adjacent the window 30*b*. Consequently, the relatively dry gas from said gas source will flow through the bleed valve 416, intermediate chamber 418, first main valve 412 and flow passage 410. The direction of flow of the gas will be determined by at what location the gas source is connected to the system.

The flow of the gas from the gas source to either the bleed location or end of the flow passage 410 other than that adjacent the window 30*b* will result in any relatively wet atmospheric gas which is present adjacent the window 30*b* being purged from the system and replaced by the relatively dry gas from the gas source. Consequently, condensation caused by the atmospheric gas on the window 30*b* will be reduced and/or eliminated. Once the relatively wet atmospheric gas has been removed from the system such that it is no longer adjacent the window 30*b*, the double block and bleed valve assembly 402 and flow passage 410 can be returned to their normal operating conditions.

It will be appreciated that some embodiments will include a heater assembly, vent passage and double block and bleed valve assembly as shown. Other embodiments may not include a heater assembly and/or a double block and bleed valve assembly. A vent passage, heater assembly, and/or double block and bleed assembly as described above may be incorporated in any of the embodiments optical chemical analyser and/or liquid depth sensor as discussed within this document.

Referring once again to FIG. 11, the previously described optical chemical analysers include an optics module which is configured to direct the first amount of radiation 200 so that the first amount of radiation passes through free space immediately before being incident on the target. This is to say, if—as shown in FIG. 11—the target is a liquid formed within the gas pipeline 10, then the first amount of radiation 200 will pass through free space (in this case a fluid in the form of a gas, although it may be any appropriate fluid) immediately before it is incident on the target liquid 14. Likewise, the optics module is configured such that the second amount of radiation 206 from the target (in this case liquid 14) passes through the free space (i.e., fluid—in this case gas, although in other embodiments it may be any appropriate fluid) prior to the second amount of radiation being provided to the SIFT module.

The fluid (which in this case is gas) is located directly adjacent to the target (liquid 14).

In certain applications it may be advantageous to be able to determine the presence or size of any liquid or particulate aerosol which is present within a gas within the vessel to which an optical chemical analyser or liquid depth sensor is mounted.

For example, in certain applications (for example if the vessel is a gas pipeline) although the gas may contain a contaminant (for example a liquid), unless the contaminant is in an aerosol form it may not cause any significant damage to certain types of machinery attached to the pipeline. For example, if liquid contaminants are present but have collected at the bottom of the gas pipeline and are not being transported with the flow of the gas, then it is unlikely that the liquid contaminants will reach any machinery via the gas pipeline and therefore the presence of such liquid contaminant may not be of immediate concern. Consequently, some embodiments of the optical chemical analyser may include an aerosol detection module to detect when aerosols are present. If aerosols are detected then this may serve as a warning that the aerosols may adversely affect machinery which is connected to the pipeline.

The aerosol detection module is configured to compare an intensity of an amount of radiation which is directed at a fluid (for example the gas within a gas pipeline) before it is incident on the fluid, with an intensity of a portion of the amount of radiation which is back-scattered by the fluid. By comparing the intensity of the radiation before it is incident on the fluid and the intensity of the radiation which is back-scattered by the fluid, it may be possible to provide a measure indicative of the amount of aerosol within the fluid. For example, in some embodiments, by comparing the intensity of the radiation before it is incident on the fluid and the amount of radiation which is back-scattered by the fluid, it may be possible to provide an indication as to the presence or otherwise of an aerosol within the fluid.

In some embodiments the amount of radiation which is directed at the fluid may be the first amount of radiation (i.e. that which is produced by the radiation source of the optical chemical analyser). In some embodiments the amount of radiation which is directed at the fluid may be the first amount of detection radiation which is produced by the radiation source of the liquid depth sensor.

In some embodiments the aerosol detection module may include an independent source of radiation (indicated as 410 in FIG. 5) which is directed into the fluid. The aerosol detection module measures the amount of radiation which is scattered by the fluid using a detector (indicated as 412 in FIG. 5). The detector provides a detector signal to the microprocessor 52 which is indicative of the amount of scatter radiation incident on the detector. By measuring the amount of the radiation directed into the fluid that is scattered by the fluid the processor 52 may determine a measure indicative of the quantity of aerosol present in the fluid as discussed below.

Furthermore, in some embodiments, the aerosol detection module may only measure the amount of radiation which is scattered by the fluid using a detector). That is to say, in these embodiments, the aerosol detection module does not measure the intensity of the radiation which is directed into the fluid.

The presence of liquid or particulate aerosol within the gas contained within the vessel will increase the amount of scatter compared to when there is no liquid or particulate aerosol present within the gas at all. This is because liquid and particulate aerosols cause a greater scattering of light than gas. There are many factors which contribute to the amount of scattering produced by a liquid or particulate aerosol and these are not explained in detail as it is not important in understanding the functioning of the aerosol detection module. Examples of factors which may affect the amount an aerosol scatters radiation include the number concentration of aerosol particles, the surface area of the aerosol particles, the substance of the aerosol particles and the mass of the aerosol particles.

The aerosol detection module may operate in one of two different manners. In the first manner the amount of radiation which is directed at the fluid is focused towards a focus position at the bottom of the vessel (e.g. pipeline). In this case such there is a relatively large path back-scattered radiation from the focus position has to travel via the fluid so as to be detected. In this case, the presence of an aerosol will cause a decrease in the measured intensity of the portion of the amount of radiation which is back-scattered by the fluid. This is because, radiation which is back-scattered at the focus position of the radiation has to travel back to a detector for detecting the back-scatter amount of radiation through the fluid containing an aerosol which causes scattering. The radiation which is back-scattered may be further scattered by the aerosol within the fluid such that less of the radiation which is back-scattered by the fluid at the focus position reaches the detector and therefore can be measured.

In an aerosol detection module operating in a second manner, the amount of radiation which is directed at the fluid is focused at a focus position which is approximately at the middle of the vessel (e.g. gas pipeline) such that there is a relatively short path for the portion of the amount of radiation which is back-scattered at the focus position to travel through the fluid so as to be detected. An increase in the presence of aerosol within the fluid will cause more radiation to be back-scattered at the focus position. Due to the fact that the back-scattered radiation only has to travel a relatively short distance through the fluid containing the scattering aerosol, a relatively large portion of the back-scattered radiation reaches the detector. Consequently, an aerosol detector operating in this manner (i.e. where the amount of radiation directed at the fluid is incident at a position which is approximately at the centre of the vessel) an increase in aerosol within the fluid will result in an increase in measured intensity of back-scattered radiation.

Within the previously described aerosol detectors, the focus position of the amount of radiation directed at the fluid in the first manner has a longer path length through the fluid to the detector which detects the intensity of the amount of radiation which is back-scattered compared to the path length through the fluid between the focus position of the radiation directed at the fluid in the second manner and the detector.

Figure 14:
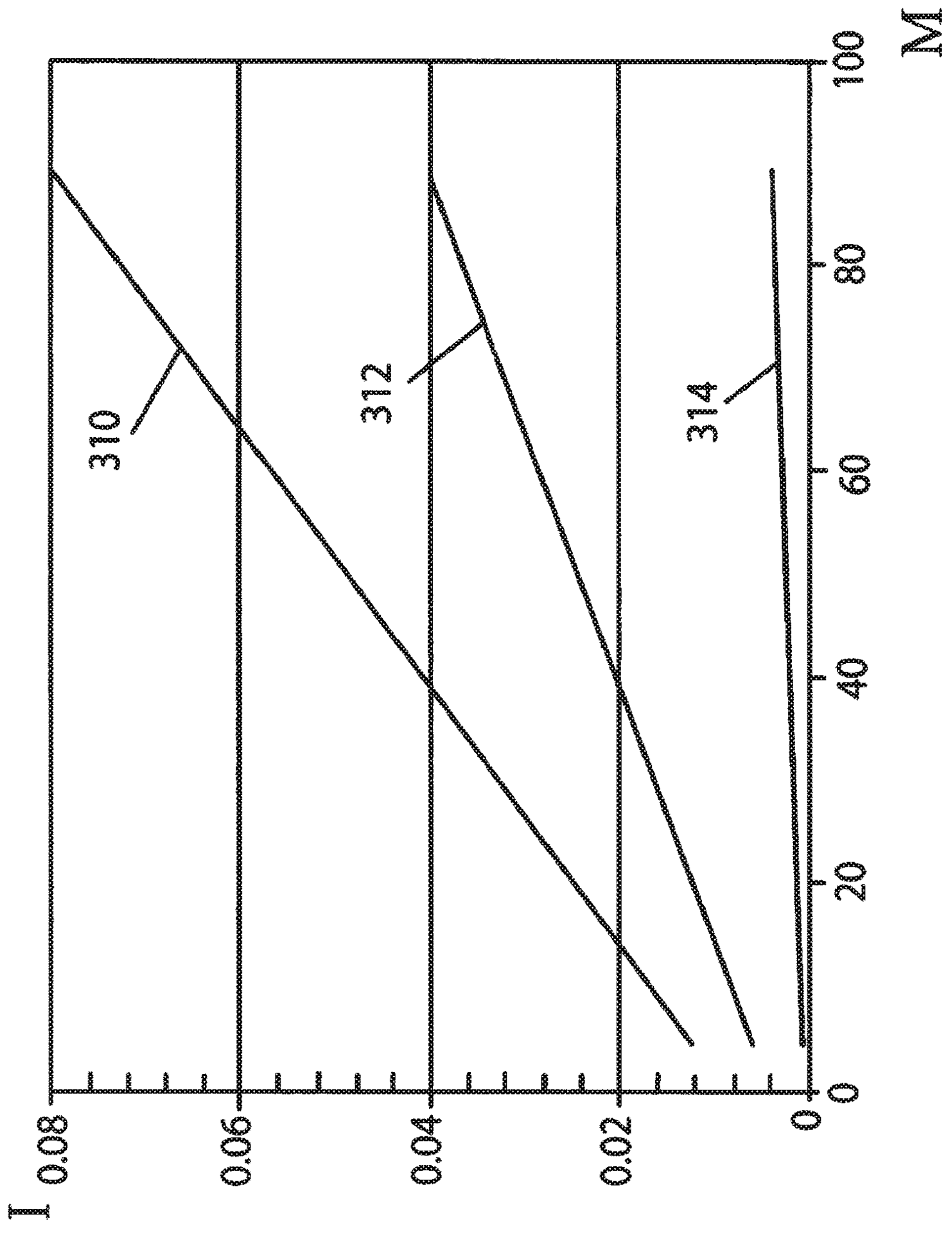
FIG. 14 shows a graph of change in measured intensity (I) against mass of aerosol particles (M) for several diameters of aerosol particles, the intensity being measured by an aerosol detection module which may form part of an embodiment of the present invention.

FIG. 14 shows a graph of the percentage increase in the detected intensity of back-scattered radiation I against increase in particle mass M measured in μg. The percentage increase in the intensity of the back-scattered radiation as a function of the increase in particle mass is shown for three different diameters are aerosol particle. 310 shows the percentage change in signal for 0.5 μm particles. 312 shows the percentage change in signal for 1 μm particles. 314 shows the percentage change in signal for 10 μm particles.

The results shown in graph of FIG. 14 were taken using an aerosol module which directs an amount of radiation into the fluid (in this case gas) such that the focus position is approximately in the middle of the vessel. It can be seen that either a change in particle size of an aerosol or a change in the mass of aerosol particles can produce a change in the intensity of back-scattered radiation which can be measured.

A controller may be configured to determine a measure indicative of the quantity of aerosol present within the gas. The controller may be configured to output a signal which is a function of the measure indicative of the quantity of aerosol present within the gas. For example, the controller may output an aerosol present signal if the detected amount of back-scattered radiation is greater than a predetermined value (if the amount of radiation directed into the fluid is focused approximately at the centre of the vessel and fluid) or below a predetermined value (if the amount of radiation directed at the fluid is focused at a portion of the vessel/fluid which is near to the bottom of the vessel).

Within the previously described embodiments of optical chemical analyser and liquid depth sensor the vessel has been a gas pipeline and the target has been a liquid contaminant present within the gas pipeline. It will be appreciated that in other embodiments, the vessel may be any appropriate vessel capable of holding a fluid. The fluid may be any appropriate fluid. For example the fluid may be a liquid, for example in a liquid pipeline. The target may be a gas or liquid.

In some embodiments the vessel may be a fluid cell, and the fluid may be a liquid or a gas. Liquid or gas may be introduced to the fluid cell and subsequently analysed by the optical chemical analyser.

In some embodiments the optical chemical analyser and/or liquid depth sensor may be configured such that the target and/or depth sensing location are located at a portion of a filter arrangement. The filter arrangement may be located in a fluid conduit and may be configured to reduce the amount of a contaminant within the fluid flowing through the fluid conduit. For example, the target and/or depth sensing location may be located at a surface of a filter element of a filter arrangement, the filter element being configured to remove at least a portion of a contaminant within the fluid as the fluid flows through the filter arrangement. In some embodiments, the fluid may be a liquid, whereas in others it may be a gas. The contaminant may be one of a solid, liquid or a gas. The liquid depth sensor may be configured such that the measure indicative of the depth of the liquid which is determined by the liquid depth sensor is indicative of the level of contaminant present within the filter. For example, in some embodiments, the greater the measure indicative of the depth of the liquid, the greater the level of contaminant present within the filter. In some embodiments it may be desirable to determine the level of the containment present within the filter, because, in such embodiments, the performance of the filter may be reduced if the level of contaminant within the filter is too high. For example, if the level of contaminant within the filter is too high, the flow of fluid through the filter may be reduced in an undesirable manner. Consequently, if the liquid depth sensor measures that the level of contaminant within the filter is above a pre-determined value, it may provide an indication that the filter requires replacement in order to maintain filtration performance. In some embodiments the contaminant may include a solid and, consequently, the liquid depth detector will determine a measure indicative of the depth of said solid.

If the target of the optical chemical analyser is located at a portion of a filter arrangement, then it may be possible to determine whether a particular substance is present within the contaminant and/or identify what substance the contaminant is.

In some embodiments the optical chemical analyser and/or liquid depth sensor may be configured such that the target and/or depth sensing location are located at a portion of a drain trap. A drain trap is a portion of a vessel, such as a conduit, for example a pipeline, which is located at the lowest point of the vessel. Due to the fact that the drain trap is at the lowest point of the vessel, denser components of a fluid within the vessel will collect, by virtue of gravity, in the drain trap. If the fluid within the vessel is a gas, the denser components may be a relatively dense portion of gas, a liquid or a solid. If the fluid within the vessel is a liquid, the denser components may be a relatively dense portion of liquid or a solid. Configuring the optical chemical analyser and/or liquid depth sensor such that the target and/or depth sensing location are located at a portion of a drain trap may enable the optical chemical analyser to identify the denser components which collect in the drain trap and/or enable the liquid depth sensor to produce a measurement indicative of the depth (and hence amount) of denser components which have collected in the drain trap. In some embodiments, the denser components may be contaminants.

In some embodiments of optical chemical analyser, the target may be a process fluid (i.e. a fluid which is used as part of the industrial process). The process fluid may be held within the vessel at an elevated pressure, for example a pressure of above about two or three atmospheres.

Within the previously described embodiments of liquid depth sensor and optical chemical analyser, each has included an on-pipe unit which is secured to the vessel and an off-pipe unit, remote to the on-pipe unit which is not secured to the vessel. In some embodiments all of the components may be housed within an on-pipe unit.

Furthermore, within the described embodiments, certain components of the liquid depth sensor and certain components of the optical chemical analyser are located in the on-pipe unit or the off-pipe unit. It will be appreciated that in other embodiments, the components of the liquid detection sensor or optical chemical analyser which are located within the off-pipe unit or the on-pipe unit may vary. That is to say, some of the components shown located in the off-pipe unit may be located in the on-pipe unit and vice versa. In some embodiments there may be no off-pipe unit. For example, in some embodiments, the optical chemical analyser may be located entirely in an on-pipe unit.

The embodiments of optical chemical analyser and liquid depth sensor described all include at least one optical fibre through which portions of radiation pass. In other embodiments, at least some of the portions of radiation which pass through the at least one optical fibre in the described embodiments may pass through free space. In some embodiments, all of the portions of radiation which pass through the at least one optical fibre in the described embodiments may pass through free space. That is to say, some embodiments of optical chemical analyser and/or liquid depth detector may not comprise a fibre optic.

Due to the fact that the liquid depth sensor and optical chemical analyser are both located exterior to the vessel to which they are mounted, the liquid depth sensor and optical chemical analyser do not intrude into the vessel. For example, the liquid depth sensor and optical chemical analyser do not include a probe which intrudes into the vessel. This may be advantageous in some applications. For example, in the case where the liquid depth sensor or optical chemical analyser are mounted to a gas pipeline, it may be advantageous that no portion of the optical chemical analyser or liquid depth sensor protrude into the pipeline because, on occasion, large objects may travel through the pipeline. An example or such an object which may travel through the pipeline is a cleaning pig. If such an object were to travel through the gas pipeline whilst a portion of the optical chemical analyser or liquid depth sensor was protruding into the gas pipeline, then such protruding portions may be destroyed by the pig or may otherwise obstruct the pig.

In the described embodiments in which the liquid depth sensor and optical chemical analyser are mounted to the exterior of a vessel, the various portions of radiation pass through a single window. In other embodiments this may not be the case. The various portions of radiation required by the optical chemical analyser and/or liquid depth sensor may pass through any appropriate number of windows.

In some embodiments, at least a portion of the liquid depth sensor and/or optical chemical analyser may be mounted within the spur pipe or within the pipeline. For example, some embodiments of liquid depth sensor which include a reference channel may be configured such that a portion of the reference channel is located within the vessel (e.g. on the same side of the window as the fluid contained by the vessel). In this way, the fourth and/or fifth amount of radiation which form(s) part of the reference channel pass through the fluid within the vessel and is therefore affected by the temperature of the fluid within the vessel. As such, the reference channel may be used by the controller to correct the output of the liquid depth sensor to compensate for an effect of the temperature of the vessel and/or fluid within the vessel on the measure indicative of the depth of the liquid. In other embodiments of liquid depth sensor and/or optical chemical analyser, it may be desirable for the window through which the relevant mounts of radiation pass as they enter/exit the vessel to be as small as possible. For this reason, such embodiments may include a converging element (such as a converging lens) which is located inside the vessel and which is configured to converge at least one of the amounts of radiation which passes through the window, so as to reduce the width of the radiation such that it can pass through a window of reduced size.

Although the embodiments of optical chemical analyser discussed herein relate in general to the determining the presence of a liquid substance at the target location and/or determine a concentration of a liquid substance at the target location; in other embodiments the substance at the target location may be a gas or a solid.

Although the embodiments of depth sensor discussed herein relate in general to determining a measure indicative of the depth of a liquid at a depth sensing location, in other embodiments this need not be the case. For example, in some embodiments the depth sensor may be configured to determine a measure indicative of the depth of a solid at a depth sensing location. In some examples a solid may transported in (e.g. dispersed in) a fluid. The solid may be dispersed within a gas in the form of an aerosol or the solid may be dispersed in a liquid in the form of a sol. The solid dispersed in the fluid may be deposited on a surface. In one example the solid is a hydrate dispersed in natural gas. If the surface is located at the depth sensing location of a depth sensor according to an embodiment of the present invention then the depth sensor may determine a measure indicative of the depth of the deposited solid on the surface.

The optical chemical analyser or liquid depth sensor may be suitable for use when the target location or depth sensing location is located in a high pressure environment. That is to say, in use, the target location or depth sensing location may be located in a high pressure environment. In embodiments of optical chemical analyser in which the target is located within a vessel, the environment within the vessel, in use, may be a high pressure environment. Likewise, in embodiments of liquid depth sensor in which the liquid (a measure of the depth of which is to be determined) is located within a vessel, the environment within the vessel, in use, may be a high pressure environment.

A high pressure environment may be an environment in which the pressure is greater than about 3 bar and less than about 300 bar. In other embodiments the pressure may be greater than about 300 bar. In some embodiments the pressure may be about 70 bar.

The optical chemical analyser or liquid depth sensor may be located such that, in use, the optical chemical analyser or liquid depth sensor or located at a stand-off position (or stand-off location) relative to the target location or depth sensing location. In some embodiments a stand-off position may be such that, in use, no component (e.g. optical component through which the first and second amounts of radiation pass) of the optical chemical analyser or liquid depth sensor is located within about 30 cm of the target location or depth sensing location. For example, in embodiments of optical chemical analyser or liquid depth sensor which include a window as previously discussed, the window may be located more than about 30 cm from the target location or depth sensing location in use. Furthermore embodiments of optical chemical analyser may be located such that no portion of the optics module (e.g. portion of the optics module through which the first and second amounts of radiation pass) is located, in use, within about 30 cm of the target location.

In other words, the optical chemical analyser may be configured to be located at a stand-off position relative to the target location such that the distance along the beam path (i.e. the path along which a beam of radiation travels in use) of each of the first and second amounts of radiation between the target location and any optical component of the optics module through which the first or second amounts of radiation pass in use is greater than about 30 cm. This enables an optical chemical analyser or liquid depth sensor according to an embodiment of the invention to be located some distance from the target location or depth sensing location. This may be advantageous in various applications. For example, in the case where the target location or depth sensing location is at the bottom of a gas pipeline of significant diameter, the fact that the optical chemical analyser or liquid depth sensor can be located at a stand-off position relative to the bottom of the gas pipeline means that the optical chemical analyser or liquid depth sensor can be located to the exterior of the top of the gas pipeline such that the gas pipeline in not obstructed.

Within the above described embodiments, the vessel or gas pipeline may carry natural gas or any other appropriate gas, for example, compressed air.

What is claimed is:

1. An optical chemical analyser comprising a target detection module, the target detection module being configured to detect a change in presence of a desired class of target and output a target change signal when a predetermined change in presence of the desired class of target is detected; and wherein the optical chemical analyser is configured such that at least a portion of the optical chemical analyser enters a powered-up state from a powered-down state based on the target change signal being output by the target detection module, wherein the target is contained in a pressurised vessel and the optical chemical analyser is configured to be mounted to and located exterior to the pressurised vessel.

2. An optical chemical analyser according to claim 1, wherein the at least a portion of the optical chemical analyser which enters a powered-up state from a powered-down state is a detector and/or a source of radiation configured to be incident on the target in order for the optical analyser to output a signal as a function of a chemical composition of the target.

3. An optical chemical analyser according to claim 1, wherein the target is a fluid.

4. An optical chemical analyser according to claim 3, wherein the pressurised vessel is a portion of a pipeline.

5. An optical chemical analyser according to claim 3 further comprising an imaging device.

6. An optical chemical analyser according to claim 5, wherein the imaging device is configured to produce an image of the fluid in the pressurised vessel.

7. An optical chemical analyser according to claim 5 further comprising an imaging controller, the imaging controller being configured such that it selectively energises the imaging device based on the target change signal.

8. An optical chemical analyser according to claim 1 further comprising an aerosol detection module, the aerosol detection module including a first intensity sensor configured to measure the intensity of an amount of radiation which is directed at a fluid before it is incident on the fluid, a second intensity sensor configured to measure the intensity of an amount of radiation which is backscattered by the fluid, and a processor configured to compare the intensity measured by the first intensity sensor and the intensity measured by the second intensity sensor to determine a measure indicative of the quantity of aerosol within the fluid.

9. An optical chemical analyser according to claim 1, wherein the optical chemical analyser comprises:

a source of a first amount of radiation, an optics module configured to direct the first amount of radiation such that it is incident on or passes through a target at a target location, the optics module further being configured to receive a second amount of radiation from the target and direct the second amount of radiation to a Spatial Interference Fourier Transform (SIFT) module, the SIFT module including a first dispersive element and a second dispersive element, the SIFT module being configured such that a portion of the second amount of radiation is received by the first dispersive element and interferes with a portion of the second amount of radiation received by the second dispersive element to form an interference pattern; the SIFT module further comprising a detector configured to capture an image of at least a portion of the interference pattern and produce a detector signal based on the captured image; and a processor configured to receive the detector signal from the detector and perform a Fourier transform on the detector signal to thereby obtain a frequency spectrum of the second amount of radiation.

10. An optical chemical analyser according to claim 9, wherein the first amount of radiation is substantially polychromatic; and wherein the SIFT module further comprises a third dispersive element and a fourth dispersive element, the SIFT module being configured such that a portion of the first amount of radiation is received by the third dispersive element and interferes with a portion of the first amount of radiation received by the fourth dispersive element to form a second interference pattern; the SIFT module further comprising a second detector configured to capture an image of at least a portion of the second interference pattern and produce a second detector signal based on the image captured by the second detector; and a processor configured to receive the second detector signal from the second detector and perform a Fourier transform on the second detector signal to thereby obtain a frequency spectrum of the first amount of radiation, the processor further being configured to compare the frequency spectrum of the second amount of radiation to frequency spectrum of the first amount of radiation in order to produce an absorption spectrum.

11. An optical chemical analyser according to claim 10, wherein the processor is configured to process the frequency spectrum of the absorption spectrum and thereby identify the presence of a substance in the target and/or determine a concentration of a substance in the target.

12. An optical chemical analyser according to claim 9, wherein the first amount of radiation is substantially monochromatic and substantially coherent.

13. An optical chemical analyser according to claim 12, wherein the second amount of radiation is Raman scattered radiation.

14. An optical chemical analyser according to claim 12, wherein the optics module further comprises a suppression filter configured to substantially prevent a component of the second amount of radiation which has a frequency which is substantially the same as a frequency of the first amount of radiation from reaching the SIFT module.

15. An optical chemical analyser according to claim 9, wherein the processor is configured to process the frequency spectrum of the second amount of radiation and thereby identify the presence of a substance in the target and/or determine a concentration of a substance in the target.

16. An optical chemical analyser according to claim 9, wherein the optics module includes an optical fibre along which the first and second amounts of radiation are transmitted.

17. An optical chemical analyser according to claim 16, further comprising a first optical filter located at a first end of the optical fibre and a second optical filter located at the second end of the optical fibre, wherein the first optical filter is selected from the group consisting of an optical band pass filter, an optical band stop filter and an optical edge filter; and wherein the second optical filter is selected from the group consisting of an optical band pass filter, an optical band stop filter and an optical edge filter; and wherein the first and second optical filters are configured to receive radiation and orientated such that an optical axis of each of the first and second optical filters is non-parallel with respect to an optical axis of the received radiation.

18. An optical chemical analyser according to claim 9, wherein the SIFT module comprises a beam splitting apparatus configured to split the second amount of radiation into: the portion of the second amount of radiation that is received by the first dispersive element, and the portion of the second amount of radiation received by the second dispersive element.

19. An optical chemical analyser according to claim 18, wherein the first and second dispersive elements are first and second diffraction gratings respectively and wherein the plane of each of the first and second diffraction gratings is non-perpendicular with respect to an optical axis of the portions of the second amount of radiation that are received by the first and second diffraction gratings respectively.

20. The optical chemical analyser of claim 9, wherein the pressurised vessel is a gas pipeline, and wherein the processor is further configured to detect the presence of a contaminant above a predetermined concentration based on the frequency spectrum, wherein the target detection module is configured to output a substance present signal when the processor detects the presence of the contaminant above the predetermined concentration.

21. The optical chemical analyser of claim 20, wherein the processor is connected to a remote terminal, and wherein the substance present signal is in the form of an alarm signal provided to the remote terminal, wherein the remote terminal is configured to receive the alarm signal and inform a user that the contaminant is present within the gas pipeline.

22. A method of operating an optical chemical analyser, the optical chemical analyser comprising a target detection module, the method comprising: the target detection module detecting a change in presence of a desired class of target; the target detection module outputting a target change signal when a predetermined change in presence of the desired class of target is detected; and at least a portion of the optical chemical analyser entering a powered-up state from a powered-down state based on the target change signal being output by the target detection module, wherein the target is contained in a pressurised vessel and the optical chemical analyser is configured to be mounted to and located exterior to the pressurised vessel.

* * * * *